(12) United States Patent
Koike et al.

(10) Patent No.: US 7,718,809 B2
(45) Date of Patent: *May 18, 2010

(54) CHROMANE SUBSTITUTED BENZIMIDAZOLE DERIVATIVES AS ACID PUMP ANTAGONISTS

(75) Inventors: Hiroki Koike, Chita-gun (JP); Sachiko Sakakibara, Chita-gun (JP)

(73) Assignee: RaQualia Pharma Inc., Aichi-ken (JP)

( * ) Notice: Subject to any disclaimer, the term of this patent is extended or adjusted under 35 U.S.C. 154(b) by 185 days.

This patent is subject to a terminal disclaimer.

(21) Appl. No.: 11/916,671

(22) PCT Filed: Jun. 2, 2006

(86) PCT No.: PCT/IB2006/001567

§ 371 (c)(1),
(2), (4) Date: Dec. 6, 2007

(87) PCT Pub. No.: WO2006/134460

PCT Pub. Date: Dec. 21, 2006

(65) Prior Publication Data

US 2008/0214519 A1 Sep. 4, 2008

Related U.S. Application Data

(60) Provisional application No. 60/690,626, filed on Jun. 14, 2005.

(51) Int. Cl.
*A61K 31/4184* (2006.01)
*C07D 405/12* (2006.01)

(52) U.S. Cl. .................... 548/304.4; 514/394
(58) Field of Classification Search ........... 548/304.4
See application file for complete search history.

(56) References Cited

U.S. PATENT DOCUMENTS

| | | | |
|---|---|---|---|
| 5,106,862 A | 4/1992 | Briving et al. | 514/394 |
| 6,465,505 B1 | 10/2002 | Amin et al. | 514/394 |

FOREIGN PATENT DOCUMENTS

| | | |
|---|---|---|
| EP | 0266326 | 3/1993 |
| WO | WO 9747603 | 12/1997 |
| WO | WO 2004054984 | 7/2004 |

OTHER PUBLICATIONS

Thomas A. Godwin, Gastrointestinal Diseases, http://edcenter.med.cornell.edu/CUMC_PathNotes/Gastrointestinal/Gastrointestinal.html, Aug. 2004, 51 pages.*
International Search Report for PCT/IB2006/001567, 6 pages, Aug. 2006.
Written Opinion by International Searching Authority for PCT/IB2006/001567, 6 pages, Dec. 2007.

* cited by examiner

*Primary Examiner*—Laura L. Stockton
(74) *Attorney, Agent, or Firm*—Scully, Scott, Murphy & Presser, P.C.

(57) ABSTRACT

This invention relates to compounds of the formula (I): or a pharmaceutically acceptable salt thereof, wherein: A, B, X, $R^1$, $R^2$, $R^3$, $R^4$, $R^5$ and $R^6$, $R^7$, $R^8$ and $R^9$ are each as described herein or a pharmaceutically acceptable salt, and compositions containing such compounds and the use of such compounds in the treatment of a condition mediated by acid pump antagonistic activity such as, but not limited to, as gastrointestinal disease, gastroesophageal disease, gastroesophageal reflux disease (GERD), peptic ulcer, gastric ulcer, duodenal ulcer, NSAID-induced ulcers, gastritis, infection of *Helicobacter pylori*, dyspepsia, functional dyspepsia, Zollinger-Ellison syndrome, non-erosive reflux disease (NERD), visceral pain, heartburn, nausea, esophagitis, dysphagia, hypersalivation, airway disorders or asthma.

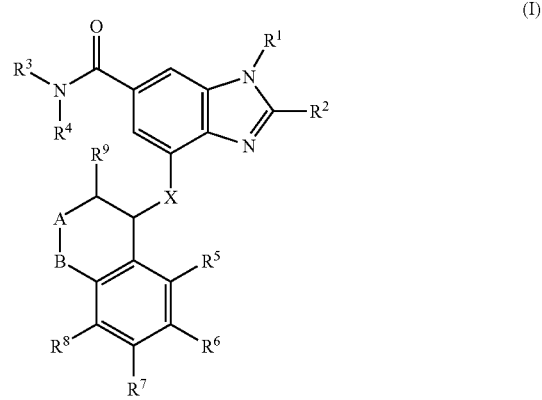

(I)

5 Claims, No Drawings

CHROMANE SUBSTITUTED BENZIMIDAZOLE DERIVATIVES AS ACID PUMP ANTAGONISTS

BACKGROUND OF THE INVENTION

This invention relates to chromane substituted benzimidazole derivatives. These compounds have selective acid pump inhibitory activity. The present invention also relates to a pharmaceutical composition, method of treatment and use, comprising the above derivatives for the treatment of disease conditions mediated by acid pump modulating activity; in particular acid pump inhibitory activity.

It has been well established that proton pump inhibitors (PPIs) are prodrugs that undergo an acid-catalyzed chemical rearrangement that permits them to inhibit $H^+/K^+$-ATPase by covalently biding to its Cystein residues (Sachs, G. et. al., *Digestive Diseases and Sciences*, 1995, 40, 3S-23S; Sachs et. al., *Annu Rev Pharmacol Toxicol*, 1995, 35, 277-305.). However, unlike PPIs, acid pump antagonists inhibit acid secretion via reversible potassium-competitive inhibition of $H^+/K^+$-ATPase. SCH28080 is one of such reversible inhibitors and has been studied extensively. Other newer agents (revaprazan, soraprazan, AZD-0865 and CS-526) have entered in clinical trials confirming their efficacy in human (Pope, A.; Parsons, M., *Trends in Pharmacological Sciences*, 1993, 14, 323-5; Vakil, N., *Alimentary Pharmacology and Therapeutics*, 2004, 19, 1041-1049). In general, acid pump antagonists are found to be useful for the treatment of a variety of diseases, including gastrointestinal disease, gastroesophageal disease, gastroesophageal reflux disease (GERD), peptic ulcer, gastric ulcer, duodenal ulcer, non-steroidal anti-inflammatory drug(NSAID)-induced ulcers, gastritis, infection of Helicobacter pylori, dyspepsia, functional dyspepsia, Zollinger-Ellison syndrome, non-erosive reflux disease (NERD), visceral pain, heartburn, nausea, esophagitis, dysphagia, hypersalivation, airway disorders or asthma(Kiljander, Toni O, *American Journal of Medicine*, 2003, 115(Suppl. 3A), 65S-71S.).

WO04/054984 discloses compounds reported to be acid pump antagonists. They refer to certain compounds having a benzimidazole structure.

There is a need to provide new acid pump antagonists that are good drug candidates and address unmet needs by PPIs for treating diseases. In particular, preferred compounds should bind potently to the acid pump whilst showing little affinity for other receptors and show functional activity as inhibitors of acid-secretion in stomach. They should be well absorbed from the gastrointestinal tract, be metabolically stable and possess favorable pharmacokinetic properties. They should be non-toxic. Furthermore, the ideal drug candidate will exist in a physical form that is stable, non-hygroscopic and easily formulated.

SUMMARY OF THE INVENTION

In this invention, it has now been found out that the new class of compounds having a chromane moiety show acid pump inhibitory activity and favorable properties as drug candidates, and thus are useful for the treatment of disease conditions mediated by acid pump inhibitory activity such as gastrointestinal disease, gastroesophageal disease, GERD, peptic ulcer, gastric ulcer, duodenal ulcer, NSAID-induced ulcers, gastritis, infection of *Helicobacter pylori*, dyspepsia, functional dyspepsia, Zollinger-Ellison syndrome, NERD, visceral pain, heartburn, nausea, esophagitis, dysphagia, hypersalivation, airway disorders or asthma (hereinafter, referred as "APA Diseases").

The present invention provides a compound of the following formula (I):

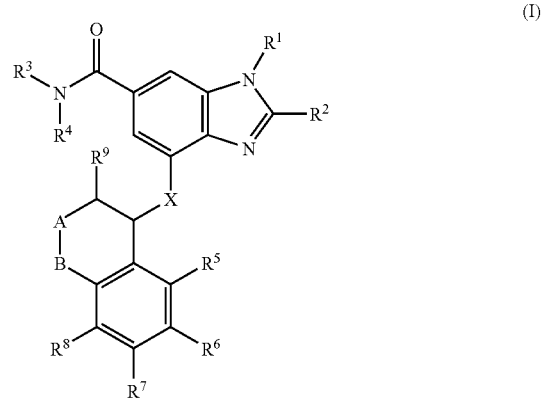

(I)

or a pharmaceutically acceptable salt thereof, wherein:
-A-B— represents —O—$CH_2$—, —S—$CH_2$—, —$CH_2$—O— or —$CH_2$—S—;
X represents an oxygen atom or NH;
$R^1$ and $R^2$ independently represent a $C_1$-$C_4$ alkyl group being unsubstituted or substituted with 1 to 2 substituents independently selected from the group consisting of a hydroxy group and a $C_1$-$C_4$ alkoxy group;
$R^3$ and $R^4$ independently represent a hydrogen atom, a $C_1$-$C_4$ alkyl group or a $C_3$-$C_7$ cycloalkyl group, said $C_1$-$C_4$ alkyl group and said $C_3$-$C_7$ cycloalkyl group being unsubstituted or substituted with 1 to 3 substituents independently selected from the group consisting of a halogen atom, a hydroxy group, a $C_1$-$C_4$ alkoxy group and a $C_3$-$C_7$ cycloalkyl group; or $R^3$ and $R^4$ taken together with the nitrogen atom to which they are attached form a 4 to 6 membered heterocyclic group being unsubstituted or substituted with 1 to 3 substituents selected from the group consisting of a hydroxy group, a $C_1$-$C_4$ alkyl group, a $C_1$-$C_4$ acyl group and a hydroxy-$C_1$-$C_4$ alkyl group;
$R^5$, $R^6$, $R^7$ and $R^8$ independently represent a hydrogen atom, a halogen atom, a hydroxy group, a $C_1$-$C_4$ alkyl group or a $C_1$-$C_4$ alkoxy group; and
$R^9$ represents a hydrogen atom, a hydroxy group or a $C_1$-$C_4$ alkoxy group.

Also, the present invention provides the use of a compound of formula (I) or a pharmaceutically acceptable salt thereof, each as described herein, for the manufacture of a medicament for the treatment of a condition mediated by acid pump modulating activity; in particular, acid pump inhibitory activity.

Preferably, the present invention also provides the use of a compound of formula (I) or a pharmaceutically acceptable salt thereof, each as described herein, for the manufacture of a medicament for the treatment of diseases selected from APA Diseases.

Also, the present invention provides a pharmaceutical composition comprising a compound of formula (I) or a pharmaceutically acceptable salt thereof, each as described herein, together with a pharmaceutically acceptable carrier for said compound.

Also, the present invention provides a pharmaceutical composition comprising a compound of formula (I) or a pharmaceutically acceptable salt thereof, each as described herein, together with a pharmaceutically acceptable carrier for said compound and other pharmacologically active agent(s).

Further, the present invention provides a method of treatment of a condition mediated by acid pump inhibitory activity, in a mammalian subject including a human, which comprises administering to a mammal in need of such treatment a therapeutically effective amount of a compound of formula (I) or a pharmaceutically acceptable salt thereof, each as described herein.

Examples of conditions mediated by acid pump inhibitory activity include, but are not limited to, APA Diseases.

The compounds of the present invention may show good bioavailability, less toxicity, good absorption, distribution, good solubility, less protein binding affinity other than acid pump, less drug-drug interaction, and good metabolic stability.

DETAILED DESCRIPTION OF THE INVENTION

In the compounds of the present invention:

Where $R^1$, $R^2$, $R^3$, $R^4$, $R^5$, $R^6$, $R^7$ and $R^8$ are the $C_1$-$C_4$ alkyl group, this $C_1$-$C_4$ alkyl group may be a straight or branched chain group having one to four carbon atoms, and examples include, but are not limited to, a methyl, ethyl, propyl, isopropyl, butyl, isobutyl, sec-butyl and tert-butyl group. Of these, a $C_1$-$C_3$ alkyl group is preferred; a $C_1$-$C_2$ alkyl group is further preferred; a methyl group is particularly preferred.

Where $R^3$ and $R^4$ and the subsistent of $R^3$ and $R^4$ are the $C_3$-$C_7$ cycloalkyl group, this represents a cycloalkyl group having three to seven carbon atoms, and examples include a cyclopropyl, cyclobutyl, cyclopentyl, cyclohexyl and cycloheptyl group. Of these, a $C_3$-$C_5$ cycloalkyl group is preferred; a cyclopropyl group is more preferred.

Where $R^3$ and $R^4$ taken together with the nitrogen atom to which they are attached form a 4 to 6 membered heterocyclic group, this 4 to 6 membered heterocyclic group represents a saturated heterocyclic group having three to five ring atoms selected from carbon atom, nitrogen atom, sulfur atom and oxygen atom other than the said nitrogen atom, and examples include, but are not limited to, a pyrrolidinyl, imidazolidinyl, pyrazolidinyl, piperidinyl, piperazinyl, morpholino, thiomorpholino, azetidinyl. Of these, a pyrrolidinyl, azetidinyl and piperazinyl group are more preferred.

Where the substituent of the 4 to 6 membered heterocyclic group is the hydroxy-$C_1$-$C_4$ alkyl group, this represents the said $C_1$-$C_4$ alkyl group substituted with a hydroxy group, and examples include, but are not limited to, a hydroxymethyl, 2-hydroxyethyl, 1-hydroxyethyl, 3-hydroxypropyl, 2-hydroxypropyl, 2-hydroxy-1-methylethyl, 4-hydroxybuthyl, 3-hydroxybuthyl, 2-hydroxybuthyl, 3-hydroxy-2-methylpropyl and 3-hydroxy-1-methylpropyl group. Of these, a hydroxy-$C_1$-$C_2$ alky group is preferred; a hydroxymethyl group is more preferred.

Where the substituent of the 4 to 6 membered heterocyclic group is the $C_1$-$C_4$ acyl group, this represents a carbonyl group substituted with the said $C_1$-$C_4$ alkyl group, and examples include, but are not limited to, a formyl, acetyl, propionyl, butyryl group. Of these, an acetyl group is preferred.

Where $R^5$, $R^6$, $R^7$, $R^8$, $R^9$ and the substituents of $R^1$ $R^2$, $R^3$ and $R^4$ are the $C_1$-$C_4$ alkoxy group, this represents an oxygen atom substituted with the said $C_1$-$C_4$ alkyl group, and examples include, but are not limited to, a methoxy, ethoxy, propoxy, isopropoxy, butoxy, isobutoxy, sec-butoxy and tert-butoxy group. Of these, a $C_1$-$C_2$ alkoxy group is preferred; a methoxy group is more preferred.

Where $R^5$, $R^6$, $R^7$, $R^8$ and the substituent of $R^3$ and $R^4$ are the halogen atom, this may be a fluorine, chlorine, bromine or iodine atom. Of these, a fluorine atom is preferred.

Where -A-B— is —O—$CH_2$— or —S—$CH_2$—, -A- corresponds —O— or —S— and —B— corresponds —$CH_2$—.

Where -A-B— is —$CH_2$—O— or —$CH_2$—S—, -A- corresponds —$CH_2$— and —B— corresponds —O— or —S—.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

Preferred compound of the present invention are those compounds of formula (I) or a pharmaceutically acceptable salt thereof, each as described herein, in which:

(A) -A-B— is —O—$CH_2$—, —S—$CH_2$—, —$CH_2$—O— or —$CH_2$—S—; X is an oxygen atom; $R^1$ and $R^2$ are independently a $C_1$-$C_4$ alkyl group being unsubstituted or substituted with 1 to 2 substituents independently selected from the group consisting of a hydroxy group and a $C_1$-$C_4$ alkoxy group; $R^3$ and $R^4$ are independently a hydrogen atom, a $C_1$-$C_4$ alkyl group or a $C_3$-$C_7$ cycloalkyl group, said $C_1$-$C_4$ alkyl group and said $C_3$-$C_7$ cycloalkyl group being unsubstituted or substituted with 1 to 3 substituents independently selected from the group consisting of a halogen atom, a hydroxy group, a $C_1$-$C_4$ alkoxy group and a $C_3$-$C_7$ cycloalkyl group; or $R^3$ and $R^4$ taken together with the nitrogen atom to which they are attached form an azetidinyl group, a pyrrolidinyl group or a piperazinyl group, said azetidinyl group, said pyrrolidinyl group and said piperazinyl group being unsubstituted or substituted with 1 to 3 substituents selected from the group consisting of a hydroxy group, a $C_1$-$C_4$ alkyl group, a $C_1$-$C_4$ acyl group and a hydroxy-$C_1$-$C_4$ alkyl group; $R^5$ and $R^7$ are independently a hydrogen atom, a halogen atom, a hydroxy group, a $C_1$-$C_4$ alkyl group or a $C_1$-$C_4$ alkoxy group; and $R^6$, $R^8$ and $R^9$ are each a hydrogen atom.

(B) -A-B— is —O—$CH_2$— or —$CH_2$—O—; X is an oxygen atom; $R^1$ and $R^2$ are independently a $C_1$-$C_2$ alkyl group; $R^3$ and $R^4$ are independently a hydrogen atom, a $C_1$-$C_3$ alkyl group being unsubstituted or substituted with a hydroxy group; or $R^3$ and $R^4$ taken together with the nitrogen atom to which they are attached form an azetidinyl group, a pyrrolidinyl group or a piperazinyl group, said azetidinyl group, said pyrrolidinyl group and said piperazinyl group being unsubstituted or substituted with 1 to 2 substituents selected from the group consisting of a hydroxy group, a $C_1$-$C_2$ alkyl group, a $C_1$-$C_2$ acyl group and a hydroxy-$C_1$-$C_2$ alkyl group; $R^5$ and $R^7$ are independently a hydrogen atom, a halogen atom or a $C_1$-$C_2$ alkyl group; and $R^6$, $R^8$ and $R^9$ are each a hydrogen atom.

(C) -A-B— is —O—$CH_2$—, —S—$CH_2$—, —$CH_2$—O— or —$CH_2$—S—; X is an oxygen atom; $R^1$ and $R^2$ are independently a $C_1$-$C_4$ alkyl group; $R^3$ and $R^4$ are independently a $C_1$-$C_4$ alkyl group being unsubstituted or substituted with 1 to 3 substituents independently selected from the group consisting of a halogen atom, a hydroxy group, a $C_1$-$C_4$ alkoxy group and a $C_3$-$C_7$ cycloalkyl group; or $R^3$ and $R^4$ taken together with the nitrogen atom to which they are attached form a pyrrolidinyl group, an azetidinyl group or a piperazinyl group, said pyrrolidinyl group, said azetidinyl group and said piperazinyl group being unsubstituted or substituted with 1 to 3 substituents selected from the group consisting of a hydroxy group, a $C_1$-$C_4$ alkyl group, a $C_1$-$C_4$ acyl group and a hydroxy-$C_1$-$C_4$ alkyl group; $R^5$, and $R^7$ are independently a hydrogen atom, a halogen atom, a hydroxy group, a $C_1$-$C_4$ alkyl group or a $C_1$-$C_4$ alkoxy group; and $R^6$, $R^8$ and $R^9$ are each a hydrogen atom.

(D) -A-B— is —O—$CH_2$— or —$CH_2$—O—; X is an oxygen atom; $R^1$ and $R^2$ are independently a $C_1$-$C_4$ alkyl group; $R^3$ and $R^4$ are independently a $C_1$-$C_4$ alkyl group being unsubstituted or substituted with 1 to 3 substituents independently selected from the group consisting of a hydroxy group and a $C_1$-$C_4$ alkoxy group; or $R^3$ and $R^4$ taken together with the nitrogen atom to which they are attached form a pyrrolidinyl group being unsubstituted or substituted with 1 to 2 substituents selected from the group consisting of a hydroxy group and a hydroxy-$C_1$-$C_4$ alkyl group; $R^5$ and $R^7$ are independently a hydrogen atom, a halogen atom, a hydroxy group a $C_1$-$C_4$ alkyl group or a $C_1$-$C_4$ alkoxy group; and $R^6$, $R^8$ and $R^9$ are each a hydrogen atom.

(E) -A-B— is —O—$CH_2$— or —$CH_2$—O—; X is an oxygen atom; $R^1$ and $R^2$ are independently a $C_1$-$C_2$ alkyl group; $R^3$ and $R^4$ are independently a $C_1$-$C_3$ alkyl group being unsubstituted or substituted with 1 to 3 substituents independently selected from the group consisting of a hydroxy group and a $C_1$-$C_2$ alkoxy group; or $R^3$ and $R^4$ taken together with the nitrogen atom to which they are attached form a pyrrolidinyl group being unsubstituted or substituted with 1 to 3 substituents selected from the group consisting of a hydroxy group and a hydroxy-$C_1$-$C_2$ alkyl group; $R^5$ and $R^7$ are independently a hydrogen atom, a halogen atom, a hydroxy group or $C_1$-$C_2$ alkyl group; and $R^6$, $R^8$ and $R^9$ are each a hydrogen atom.

(F) -A-B— is —$CH_2$—O— or —$CH_2$—S—; X is an oxygen atom; $R^1$ and $R^2$ are independently a $C_1$-$C_2$ alkyl group being unsubstituted or substituted with 1 to 2 substituents independently selected from the group consisting of a hydroxy group and a $C_1$-$C_2$ alkoxy group; $R^3$ and $R^4$ are independently a $C_1$-$C_2$ alkyl group; or $R^3$ and $R^4$ taken together with the nitrogen atom to which they are attached form a pyrrolidinyl group being unsubstituted or substituted with 1 to 2 substituents selected from the group consisting of a hydroxy group and a hydroxy-$C_1$-$C_2$ alkyl group; $R^5$ and $R^7$ are independently a hydrogen atom, a halogen atom, a hydroxy group or $C_1$-$C_2$ alkyl group; and $R^6$, $R^8$ and $R^9$ are each a hydrogen atom.

(G) -A-B— is —O—$CH_2$— or —$CH_2$—O—; X is an oxygen atom; $R^1$ and $R^2$ are independently a $C_1$-$C_4$ alkyl group being unsubstituted or substituted with 1 to 2 substituents independently selected from the group consisting of a hydroxy group and a $C_1$-$C_4$ alkoxy group; $R^3$ and $R^4$ are independently a $C_1$-$C_2$ alkyl group being unsubstituted or substituted with 1 to 3 substituents independently selected from the group consisting of a hydroxy group and a $C_1$-$C_4$ alkoxy group; $R^5$ is a $C_1$-$C_4$ alkyl group; and $R^6$, $R^7$, $R^8$ and $R^9$ are each a hydrogen atom.

(H) -A-B— is —O—$CH_2$— or —$CH_2$—O—; X is an oxygen atom; $R^1$ and $R^2$ are independently a $C_1$-$C_4$ alkyl group; $R^3$ and $R^4$ are independently a $C_1$-$C_4$ alkyl group being unsubstituted or substituted with 1 to 3 substituents independently selected from the group consisting of a halogen atom, a hydroxy group, a $C_1$-$C_4$ alkoxy group and a $C_3$-$C_7$ cycloalkyl group; $R^5$ is a hydrogen atom or a halogen atom; $R^7$ is a halogen atom; and $R^6$, $R^8$ and $R^9$ are each a hydrogen atom.

(I) -A-B— is —O—$CH_2$— or —$CH_2$—O—; X is an oxygen atom; $R^1$ and $R^2$ are independently a $C_1$-$C_2$ alkyl group; $R^3$ and $R^4$ are independently a $C_1$-$C_3$ alkyl group being unsubstituted or substituted with 1 to 3 substituents independently selected from the group consisting of a hydroxy group and a $C_1$-$C_2$ alkoxy group; $R^5$ is a hydrogen atom or a halogen atom; $R^7$ is a halogen atom; and $R^6$, $R^8$ and $R^9$ are each a hydrogen atom.

(J) -A-B— is —$CH_2$—O—; X is an oxygen atom; $R^1$, $R^2$, $R^3$ and $R^4$ are each a methyl group; $R^5$ and $R^7$ are independently a hydrogen atom, a halogen atom or a methyl group; and $R^6$, $R^8$ and $R^9$ are each a hydrogen atom.

(K) -A-B— is —$CH_2$—O—; X is an oxygen atom; $R^1$ and $R^2$ are each a methyl group; $R^3$ and $R^4$ are each a methyl group; or $R^3$ and $R^4$ taken together with the nitrogen atom to which they are attached form an azetidin-1-yl group, a pyrrolidin-1-yl group, a 3-hydroxy-pyrrolidin-1-yl group or a 4-acetyl-piperazin-1-yl group; $R^5$ and $R^7$ are independently a hydrogen atom, a halogen atom or a methyl group; and $R^6$, $R^8$ and $R^9$ are each a hydrogen atom.

Preferred classes of compound of the present invention are those compounds of formula (I) or a pharmaceutically acceptable salt thereof, each as described herein, in which:

(a) -A-B— is —O—$CH_2$— or —$CH_2$—O—;
(b) $R^1$ is a $C_1$-$C_4$ alkyl group;
(c) $R^1$ is a $C_1$-$C_2$ alkyl group;
(d) $R^1$ is a methyl group;
(e) $R^2$ is a $C_1$-$C_4$ alkyl group;
(f) $R^2$ is a $C_1$-$C_2$ alkyl group;
(g) $R^2$ is a methyl group;
(h) $R^3$ is a $C_1$-$C_4$ alkyl group being unsubstituted or substituted with 1 to 2 substituents independently selected from the group consisting of a hydroxy group and a $C_1$-$C_4$ alkoxy group;
(i) $R^3$ is a $C_1$-$C_3$ alkyl group being unsubstituted or substituted with a substituent independently selected from the group consisting of a hydroxy group and a $C_1$-$C_2$ alkoxy group;
(j) $R^3$ is a $C_1$-$C_4$ alkyl group being unsubstituted or substituted with 1 to 2 hydroxy groups;
(k) $R^3$ is a $C_1$-$C_3$ alkyl group being unsubstituted or substituted with a hydroxy group;
(l) $R^3$ is a $C_1$-$C_3$ alkyl group being unsubstituted or substituted with 1 to 2 substituents independently selected from the group consisting of a hydroxy group and a $C_1$-$C_2$ alkoxy group;
(m) $R^3$ is a methyl group or 2-hydroxyethyl group;
(n) $R^4$ is a hydrogen atom or a $C_1$-$C_4$ alkyl group;
(o) $R^4$ is a $C_1$-$C_4$ alkyl group;
(p) $R^4$ is a $C_1$-$C_2$ alkyl group;
(q) $R^4$ is a methyl group;
(r) $R^3$ and $R^4$ taken together with the nitrogen atom to which they are attached form a 5 to 6 membered heterocyclic group optionally having a further a nitrogen atom, said heterocyclic group being unsubstituted or substituted with 1 to 3 substituents selected from the group consisting of a hydroxy group, a $C_1$-$C_4$ alkyl group, a $C_1$-$C_4$ acyl group and a hydroxy-$C_1$-$C_4$ alkyl group;
(s) $R^3$ and $R^4$ taken together with the nitrogen atom to which they are attached form a pyrrolidinyl group, an azetidinyl group or a piperazinyl group, said pyrrolidinyl group, said azetidiny! group and said piperazinyl group being unsubstituted or substituted with 1 to 3 substituents selected from the group consisting of a hydroxy group, a $C_1$-$C_2$ alkyl group, a $C_1$-$C_2$ acyl group and a hydroxy-$C_1$-$C_2$ alkyl group;
(t) $R^3$ and $R^4$ taken together with the nitrogen atom to which they are attached form a pyrrolidinyl group or a piperazinyl group, said pyrrolidinyl group and said piperazinyl group being unsubstituted or substituted with 1 to 3 substituents selected from the group consisting of a hydroxy group, a $C_1$-$C_2$ alkyl group, a $C_1$-$C_2$ acyl group and a hydroxy-$C_1$-$C_2$ alkyl group;

(u) $R^3$ and $R^4$ taken together with the nitrogen atom to which they are attached form a pyrrolidinyl group being unsubstituted or substituted with 1 to 3 substituents selected from the group consisting of a hydroxy group and a hydroxy-$C_1$-$C_2$ alkyl group;

(v) $R^3$ and $R^4$ taken together with the nitrogen atom to which they are attached form a pyrrolidinyl group being unsubstituted or substituted with a substituent selected from the group consisting of a hydroxy group and a 2-hydroxyethyl group;

(w) $R^3$ and $R^4$ taken together with the nitrogen atom to which they are attached form an azetidin-1-yl group, a 3-hydroxy-3-methyl-azetidin-1-yl group, a pyrrolidin-1-yl group, a 3-hydroxy-pyrrolidin-1-yl group, a 2-hydroxymethyl-pyrrolidin-1-yl group, a 4-acetyl-piperazin-1-yl group or a 4-methyl-piperazin-1-yl group;

(x) $R^3$ and $R^4$ taken together with the nitrogen atom to which they are attached form an azetidin-1-yl group, a 3-hydroxy-pyrrolidin-1-yl group or a 4-acetyl-piperazin-1-yl group;

(y) $R^5$ is a hydrogen atom, a halogen atom, a hydroxy group, a $C_1$-$C_2$ alkyl group or a $C_1$-$C_2$ alkoxy group;

(z) $R^5$ is a hydrogen atom, a halogen atom or a methyl group;

(aa) $R^5$ is a hydroxy group, a $C_1$-$C_2$ alkyl group or a $C_1$-$C_2$ alkoxy group;

(bb) $R^5$ is a hydrogen atom, a chlorine atom or a fluorine atom;

(cc) $R^5$ is a hydrogen atom or a fluorine atom;

(dd) $R^5$ is a $C_1$-$C_2$ alkyl group;

(ee) $R^5$ is a methyl group;

(ff) $R^7$ is a hydrogen atom or a halogen atom;

(gg) $R^7$ is a hydrogen atom;

(hh) $R^7$ is a chlorine atom or a fluorine atom;

(ii) $R^7$ is a fluorine atom;

(jj) $R^6$ and $R^8$ are independently a hydrogen atom or halogen atom;

(kk) $R^6$ and $R^8$ are each a hydrogen atom;

(ll) $R^9$ is a hydrogen atom, a hydroxy group or a $C_1$-$C_2$ alkoxy group;

(mm) $R^9$ is a hydrogen atom.

Of these classes of compounds, any combination among (a) to (mm) is also preferred.

One embodiment of the invention provides a compound selected from the group consisting of 4-[(7-Fluoro-3,4-dihydro-2H-chromen-4-yl)oxy]-N,N,1,2-tetramethyl-1H-benzimidazole-6-carboxamide; 4-[(5,7-Difluoro-3,4-dihydro-2H-chromen-4-yl)oxy]-N,N,1,2-tetramethyl-1H-benzimidazole-6-carboxamide; N,N,1,2-Tetramethyl-4-[(5-methyl-3,4-dihydro-2H-chromen-4-yl)oxy]-1H-benzimidazole-6-carboxamide; or a pharmaceutical acceptable salt thereof.

Pharmaceutically acceptable salts of a compound of formula (I) include the acid addition salts and base salts (including disalts) thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

Pharmaceutically acceptable salts of the compounds of formula (I) thereof include both unsolvated and solvated forms. The term "solvate" is used herein to describe a molecular complex comprising a compound of the invention and one or more pharmaceutically acceptable solvent molecules, for example, ethanol. The term 'hydrate' is employed when said solvent is water.

Pharmaceutically acceptable solvates in accordance with the invention include hydrates and solvates wherein the solvent of crystallization may be isotopically substituted, e.g. $D_2O$, $d_6$-acetone, $d_6$-DMSO.

The term "compound of the invention" or "compounds of the invention" refers to, unless indicated otherwise, a compound of formula (I) as hereinbefore defined, isomers thereof (including optical, geometric and tautomeric isomers) as hereinafter defined and isotopically-labeled compounds of formula (I).

Compounds of formula (I) containing one or more asymmetric carbon atoms can exist as two or more stereoisomers. Where the compound contains a keto moiety, tautomeric isomerism ("tautomerism") can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying examples and preparations using an appropriate isotopically-labeled reagents in place of the non-labeled reagent previously employed.

All of the compounds of the formula (I) can be prepared by the procedures described in the general methods presented below or by the specific methods described in the examples section and the preparations section, or by routine modifications thereof. The present invention also encompasses any one or more of these processes for preparing the compounds of formula (I), in addition to any novel intermediates used therein.

General Synthesis

The compounds of the present invention may be prepared by a variety of processes well known for the preparation of compounds of this type, for example as shown in the following Method A to D.

All starting materials in the following general syntheses may be commercially available or obtained by the following Method E to G or conventional methods known to those skilled in the art, such as WO 2000078751 and WO 2004054984 and the disclosures of which are incorporated herein by references.

Method A

This illustrates the preparation of compounds of formula (I).

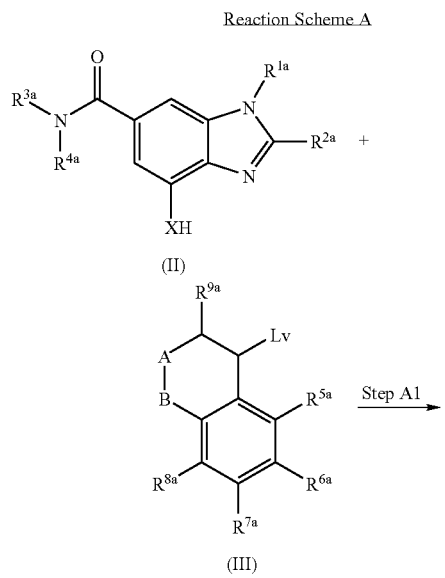

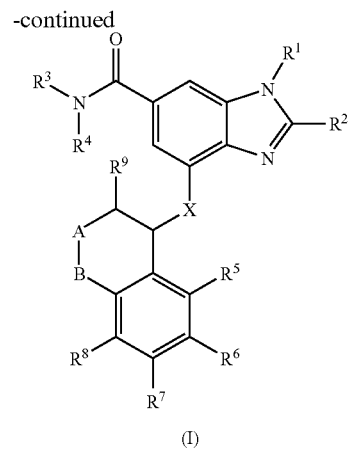

In Reaction Scheme A, $R^1$, $R^2$, $R^3$, $R^4$, $R^5$, $R^6$, $R^7$, $R^8$, $R^9$, A, B and X are each as defined above; Lv is a leaving group; $R^{1a}$ is $R^1$ as defined above or $R^1$ wherein hydroxy group is protected by a hydroxy-protecting group; $R^{2a}$ is $R^2$ as defined above or $R^2$ wherein hydroxy group is protected by a hydroxy-protecting group; $R^{3a}$ is $R^3$ as defined above or $R^3$ wherein hydroxy group is protected by a hydroxy-protecting group; $R^{4a}$ is $R^4$ as defined above or $R^4$ wherein hydroxy group is protected by a hydroxy-protecting group; $R^{5a}$ is $R^5$ as defined above or $R^5$ wherein hydroxy group is protected by a hydroxy-protecting group; $R^{6a}$ is $R^6$ as defined above or $R^6$ wherein hydroxy group is protected by a hydroxy-protecting group; $R^{7a}$ is $R^7$ as defined above or $R^7$ wherein hydroxy group is protected by a hydroxy-protecting group; $R^{8a}$ is $R^8$ as defined above or $R^8$ wherein hydroxy group is protected by a hydroxy-protecting group; and $R^{9a}$ is $R^9$ as defined above or $R^9$ wherein hydroxy group is protected by a hydroxy-protecting group; and the same shall apply hereinafter.

The term "leaving group", as used herein, signifies a group capable of being substituted by nucleophilic groups, such as a hydroxy group or amines and examples of such leaving groups include a halogen atom, a alkylsulfonyloxy group, a halogenoalkylsulfonyloxy group and a phenylsulfonyloxy group. Of these, a bromine atom, a chlorine atom, a methylsulfonyloxy group, a trifluoromethylsulfonyloxy group and a 4-methylphenylsulfonyloxy group are preferred.

The term "hydroxy-protecting groups", as used herein, signifies a protecting group capable of being cleaved by various means to yield a hydroxy group, such as hydrogenolysis, hydrolysis, electrolysis or photolysis, and such hydroxy-protecting groups are described in Protective Groups in Organic Synthesis edited by T. W. Greene et al. (John Wiley & Sons, 1999). Such as for example, $C_1$-$C_4$ alkoxycarbonyl, $C_1$-$C_4$ alkylcarbonyl, tri-$C_1$-$C_4$ alkylsilyl or tri-$C_1$-$C_4$ alkylarylsilyl groups, and $C_1$-$C_4$ alkoxy-$C_1$-$C_4$ alkyl groups. Suitable hydroxy-protecting groups include acetyl and tert-butyldimethylsilyl.

(Step A1)

In the Step A1, the compound of formula (I) is prepared by nucleophilic substitution with Lv of the compound of formula (III), which is commercially available or may be prepared by the method described in WO 2000078751, US 20050038032 or the following Method E to F, with the compound of formula (II), which is commercially available or may be prepared by the methods described in WO 2004054984.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone; or mixed solvents thereof. Of these solvents, tetrahydrofuran, N,N-dimethylformamide or ethanol is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal alkoxides, such as sodium methoxide, sodium ethoxide and potassium tert-butoxide; alkali metal carbonates, such as lithium carbonate, sodium carbonate and potassium carbonate; alkali metal hydrogencarbonates, such as lithium hydrogencarbonate, sodium hydrogencarbonate and potassium hydrogencarbonate; amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU); alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, sodium hydride, potassium carbonate or potassium tert-butoxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours, will usually suffice.

Deprotecting Step

In the case where $R^{1a}$, $R^{2a}$, $R^{3a}$, $R^{4a}$, $R^{5a}$, $R^{6a}$, $R^{7a}$, $R^{8a}$ or $R^{9a}$ has a protected hydroxy group, the deprotection reaction will follow to yield a hydroxy group. This reaction is described in detail by T. W. Greene et al., Protective Groups in Organic Synthesis, 369-453, (1999), the disclosures of which are incorporated herein by reference. The following exemplifies a typical reaction involving the protecting group tert-butyldimethylsilyl.

The deprotection of the hydroxyl groups is carried out with an acid, such as acetic acid, hydrogen fluoride, hydrogen fluoride-pyridine complex, or fluoride ion, such as tetrabutylammonium fluoride (TBAF).

The deprotection reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include, but are not limited to: alcohol, such as methanol, ethanol or mixed solvents thereof.

The deprotection reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

Method B

This illustrates the preparation of compounds of formula (I).

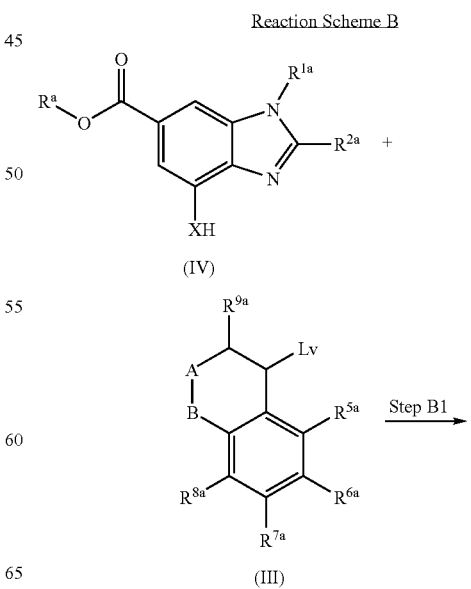

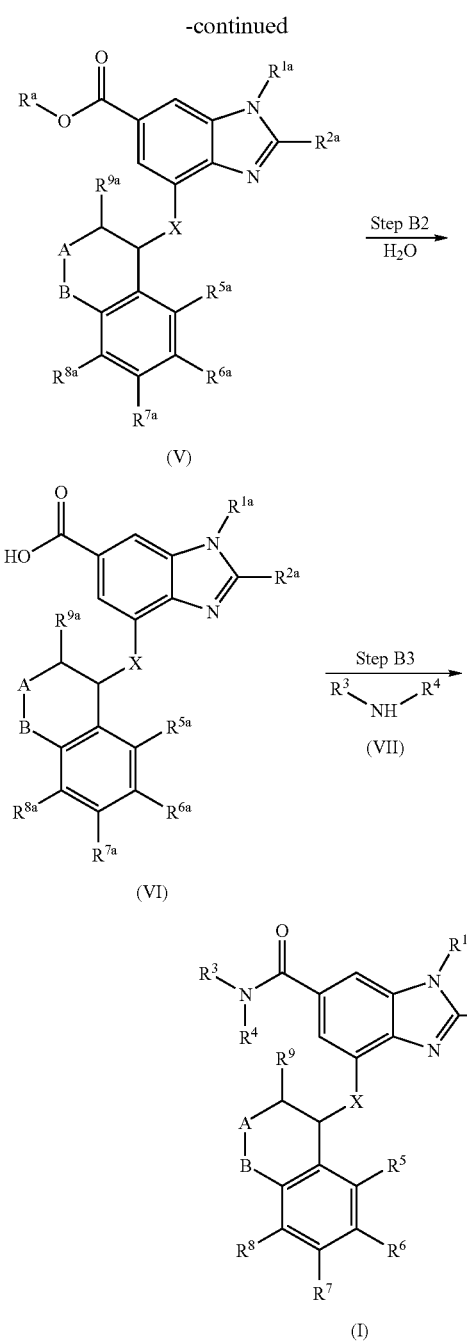

(Step B2)

In this step, the compound (VI) is prepared by hydrolysis of the ester group of the compound of formula (V) with a base or an acid.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; sulfoxides, such as dimethyl sulfoxide and sulfolane; water; or mixed solvents thereof. Of these solvents, methanol, ethanol or tetrahydrofuran is preferred.

The reaction may be carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate. Of these, lithium hydroxide or sodium hydroxide is preferred.

The reaction may be carried out in the presence of an acid. There is likewise no particular restriction on the nature of the acids used, and any acid commonly used in reactions of this type may equally be used here. Examples of such acids include: carboxylic acids, such as acetic acid or propionic acid; acids, such as hydrochloric acid, sulfuric acid or hydrobromic acid. Of these, hydrochloric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 24 hours, will usually suffice.

(Step B3)

In this step, the compound (I) is prepared by amidation of the compound of formula (VI) with the compound of formula (VII), which is commercially available. If the compound of formula (VI) or (VII) has hydroxy-protecting groups, the deprotection reaction described in Method A will be applied in an appropriate step.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; or mixed solvents thereof. Of these, N,N-dimethylformamide is preferred.

The reaction is carried out in the presence of a base. There is likewise no particular restriction on the nature of the bases In Reaction Scheme B, $R^a$ is a $C_1$-$C_4$ alkyl group or benzyl group.

(Step B1)

In this step, the compound of formula (V) is prepared by nucleophilic substitution with Lv of the compound of formula (III) which is commercially available or may be prepared by the method described in WO 2000078751 or the following Method E to F, with the compound of formula (IV), which is commercially available or may be prepared by the methods described in WO 2004054984. The reaction may be carried out under the same condition as described in Step A1 of Method A.

used, and any base commonly used in reactions of this type may equally be used here. Examples of such bases include: amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, DBN, DABCO and DBU. Of these, triethylamine or diisopropylethylamine is preferred.

The reaction is carried out in the presence of a condensing agent. There is likewise no particular restriction on the nature of the condensing agents used, and any condensing agent commonly used in reactions of this type may equally be used here. Examples of such condensing agents include: 2-halo-1-lower alkyl pyridinium halides, such as 2-chloro-1-methy pyridinium iodide and 2-bromo-1-ethylpyridinium tetrafluoroborate (BEP); diarylphosphorylazides, such as diphenylphosphorylazide (DPPA); chloroformates, such as ethyl chloroformate and isobutyl chloroformate; phosphorocyanidates, such as diethyl phosphorocyanidate (DEPC); imidazole derivatives, such as N,N'-carbonyldiimidazole (CDI); carbodiimide derivatives, such as N,N'-dicyclohexylcarbodiimide (DCC) and 1-(3-dimethylaminopropyl)-3-ethylcarbodiimide hydrochloride (EDCl); iminium salts, such as 2-(1H-benzotriazol-1-yl)-1,1,3,3-tetramethyluronium hexafluorophosphate (HBTU) and tetramethyl fluoroformamidinium hexafluoro phosphate (TFFH); and phosphonium salts, such as benzotriazol-1-yloxytris(dimethylamino)phosphonium hexafluorophosphate (BOP) and bromo-tris-pyrrolidino-phosphonium hexafluorophosphate (PyBrop). Of these, EDCl or HBTU is preferred.

Reagents, such as 4-(N,N-dimethylamino)pyridine (DMAP), and 1-hydroxybenztriazole (HOBt), may be employed for this step. Of these, HOBt is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 80° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours, will usually suffice.

Method C

This illustrates the preparation of compounds of formula (Ia) wherein X is oxygen atom.

Reaction Scheme C

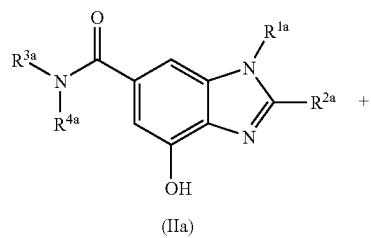

(IIa)

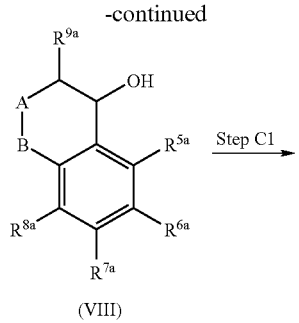

(VIII)

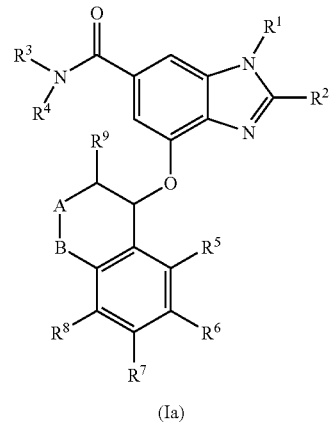

(Ia)

(Step C1)

In this step, the compound (Ia) is prepared by ether formation reaction of the compound of formula (IIa), which is commercially available or may be prepared by the methods described in WO 2004054984, with the compound (VIII), which is commercially available or may be prepared by the method described in the following Method E to F. If the compound of formula (IIa) or (VIII) has a hydroxy-protecting group, the deprotection reaction described in Method A will be applied.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; or mixed solvents thereof. Of these, tetrahydrofuran or toluene is preferred.

The reaction is carried out in the presence of a condensing agent. There is likewise no particular restriction on the nature of the condensing agents used, and any condensing agent commonly used in reactions of this type may equally be used here. Examples of such condensing agents include: azodicarboxylic acid di-lower alkyl esters, such as diethyl azodicarboxylate (DEAD), diisopropyl azodicarboxylate (DIAD) and di-tert-butyl azodicarboxylate (DTAD); azodicarboxamides, such as N,N,N',N'-tetraisopropylazodicarboxamide (TIPA), 1,1'-(azodicarbonyl)dipiperidine (ADDP) and N,N,N',N'-tetramethylazodicarboxamide (TMAD); phosphoranes, such as (cyanomethylene)tributylphosphorane (CMBP) and (cyanomethylene)trimethylphosphorane (CMMP). Of these, DIAD is preferred.

Phosphine reagents, such as triphenylphosphine, and tributylphosphine, may be employed for this step. Of these, triphenylphosphine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 120° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 48 hours, will usually suffice.

Method D

This illustrates the preparation of compounds of formula (Ib) wherein $R^9$ is a hydroxy group or a $C_1$-$C_4$ alkoxy group.

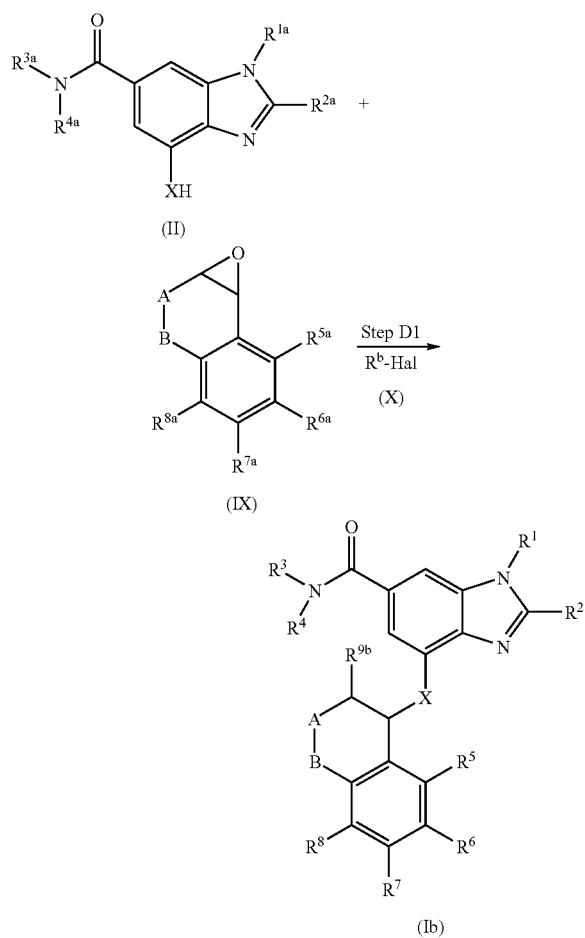

Reaction Scheme D

In Reaction Scheme D, Hal is a halogen atom, $R^b$ is a $C_1$-$C_4$ alkyl group and $R^{9b}$ is a hydroxy group or $R^b$—O—.

(Step D1)

In this step, the compound of formula (Ib) is prepared by epoxy opening reaction (D1-a) of the compound of formula (II), which is commercially available or may be prepared by the methods described in WO 2004054984, with the compound (IX), which is commercially available or can be prepared according to following Method G. After this reaction, alkylation of hydroxy group (D1-b) with the compound of formula (X) may follows. If the compound of formula (II) or (IX) has a hydroxy-protecting group, the deprotection reaction described in Method A will be applied.

(D1-a) Epoxy Opening Reaction

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone; water; or mixed solvents thereof. Of these, ethanol in corporate with water is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate; amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, DBN, DABCO and DBU. Of these, triethylamine is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 120° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 48 hours, will usually suffice.

(D1-b) Alkylation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; sulfoxides, such as dimethyl sulfoxide and sulfolane; or mixed solvents thereof. Of these, N,N-dimethylformamide is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal alkoxides, such as sodium methoxide, sodium ethoxide and potassium tert-butoxide; alkali metal amides, such as lithium amide, sodium amide, potassium amide, lithium diisopropyl amide, potassium diisopropyl amide, sodium diisopropyl amide, lithium bis(trimethylsilyl) amide and potassium bis(trimethylsilyl)amide. Of these, sodium hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 48 hours, will usually suffice.

Method E

This illustrates the preparation of compounds of formula (IIIa) wherein A is $CH_2$.

Reaction Scheme E

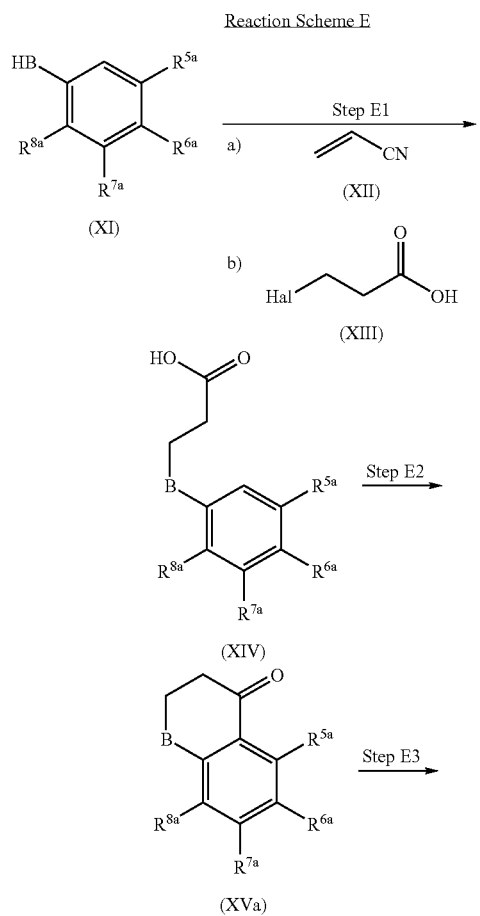

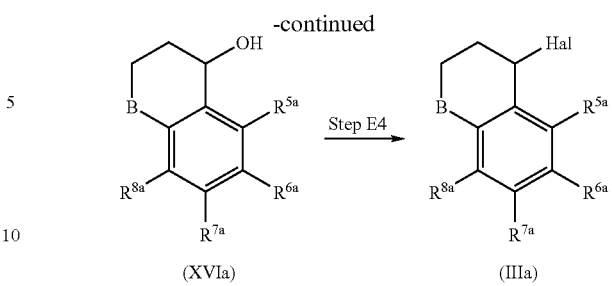

In Reaction Scheme E, Hal is a halogen atom and the same shall apply hereinafter.

(Step E1)

In this step, the compound of formula (XIV) is prepared by Michael reaction (E1-a) of the compound of formula (XI) with the compound of formula (XII) or by alkylation reaction (E1-b) of the compound of formula (XI) with the compound of formula (XIII). The compound of formula (XI), (XII) and (XIII) are commercially available.

(E1-a) Michael Reaction

The reaction is normally and preferably effected in the presence or the absence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; sulfoxides, such as dimethyl sulfoxide and sulfolane; or mixed solvents thereof. Of these, the reaction in the absence of solvent is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal alkoxides, such as sodium methoxide, sodium ethoxide and potassium tert-butoxide; alkali metal carbonates, such as lithium carbonate, sodium carbonate and potassium carbonate; amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, DBN, DABCO, DBU and benzyltrimethylammonium hydroxide; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl) amide. Of these, benzyltrimethylammonium hydroxide or sodium methoxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 120° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 48 hours, will usually suffice.

After the above procedure, hydrolysis is carried out by adding an acid in a solvent to produce the compound of formula (XIV), and may be carried out in a usual hydrolysis condition. The acid may include, for example, inorganic acids such as hydrochloric acid, hydrobromic acid and sulfuric acid. It is preferably hydrochloric acid. The solvent may include, for example, water; alcohols such as methanol, ethanol, propanol and tert-butanol; ethers such as diethyl ether, dimethoxyethane, tetrahydrofuran, diethoxymethane and dioxane; or mixed solvents thereof. It is preferably water. The reaction temperature varies depending on the starting compound, the reagent and the solvent, however, it is usually from 20° C. to the reflux temperature. The reaction time varies depending on the starting compound, the reagent, the solvent and the reaction temperature, however, it is usually from 60 minutes to 24 hours.

(E1-b) Alkylation Reaction

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; alcohols, such as methanol, ethanol, propanol, 2-propanol and butanol; nitriles, such as acetonitrile and benzonitrile; sulfoxides, such as dimethyl sulfoxide and sulfolane; ketones, such as acetone and diethylketone; water; or mixed solvents thereof. Of these, water is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal alkoxides, such as sodium methoxide, sodium ethoxide and potassium tert-butoxide; alkali metal carbonates, such as lithium carbonate, sodium carbonate and potassium carbonate; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, sodium hydroxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 100° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 24 hours, will usually suffice.

Introduction of the Hydroxy-Protecting Group

In the case of the compound of formula (IIIa) having a hydroxy group, if necessary, the reaction may be accomplished by protecting the hydroxy group.

The introduction of the hydroxy-protecting group can be carried out at an appropriate step before the reaction affected by the hydroxy group.

This reaction is described in detail by T. W. Greene et al., Protective Groups in Organic Synthesis, 369-453, (1999), the disclosures of which are incorporated herein by reference. The following exemplifies a typical reaction involving the protecting group tert-butyldimethylsilyl.

For example, when the hydroxy-protecting group is a "tert-butyldimethylsilyl", this step is conducted by reacting with a desired hydroxy-protecting group halide in an inert solvent in the presence of a base.

Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; or mixed solvents thereof. Of these, tetrahydrofuran or N,N-dimethylformamide is preferred.

Examples of the hydroxy-protecting group halide usable in the above reaction include trimethylsilyl chloride, triethylsilyl chloride, tert-butyldimethylsilyl chloride, tert-butyldimethylsilyl bromide, acetyl chloride are preferred.

Examples of the base include alkali metal hydroxides such as lithium hydroxide, sodium hydroxide and potassium hydroxide, alkali metal carbonates such as lithium carbonate, sodium carbonate and potassium carbonate, and organic amines such as triethylamine, tributylamine, N-methylmorpholine, pyridine, imidazole, 4-dimethylaminopyridine, picoline, lutidine, collidine, DBN and DBU. Out of these, triethylamine, imidazole, or pyridine is preferred. Upon use of an organic amine in the liquid form, it also serves as a solvent when used in large excess.

Although the reaction temperature differs with the nature of the starting compound, the halide and the solvent, it usually ranges from 0° C. to 80° C. (preferably 0 to 30° C.). Although the reaction time differs with the reaction temperature or the like, it ranges from 10 minutes to 2 days (preferably 30 minutes to 1 day).

(Step E2)

In this step, the compound of formula (XVa) is prepared by Friedel Crafts reaction (E2-a) after halogenation (E2-b) or by cyclization (E2-c) of the compound of formula (XIV).

(E2-a) Friedel Crafts Reaction

The reaction is normally and preferably effected in the presence or the absence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride, 1,1,2,2-tetrachloroehane and 1,2-dichloroethane; aromatic hydrocarbons, such as benzene, toluene and nitrobenzene; carbon disulfide; or mixed solvents thereof. Of these, dichloromethane or carbon disulfide is preferred.

The reaction is carried out in the presence of an acid. There is likewise no particular restriction on the nature of the acids used, and any acid commonly used in reactions of this type may equally be used here. Examples of such acids include:

Lewis acids, such as $BF_3$, $AlCl_3$, $AlBr_3$, $FeCl_3$, $AgCl$, $ZnI_2$, $ZnCl_2$, $Fe(NO_3)_3$, $CF_3SO_3Si(CH_3)_3$, $Yb(CF_3SO_3)_3$ and $SnCl_4$. Of these, $AlCl_3$ is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 150° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours, will usually suffice.

(E2-b) Halogenation

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; amides, such as formamide, N,N-dimethylformamide, N,N-dimethylacetamide and hexamethylphosphoric triamide; amines, such as nitriles, such as acetonitrile and benzonitrile; or mixed solvents thereof. Of these, 1,2-dichloroethane or dichloromethane is preferred.

The reaction is carried out in the presence of a halogenating agent. There is likewise no particular restriction on the nature of the halogenating agents used, and any halogenating agent commonly used in reactions of this type may equally be used here. Examples of such halogenating agents include: thionyl chloride, oxalyl chloride and phosphorus oxychloride. Of these, thionyl chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 80° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 8 hours will usually suffice.

(E2-c) Cyclization

The reaction is normally and preferably effected in the presence or absence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; or mixed solvents thereof. Of these, dichloromethane or the absence of solvent is preferred.

The reaction is carried out in the presence of an acid. There is likewise no particular restriction on the nature of the acids used, and any acid commonly used in reactions of this type may equally be used here. Examples of such acids include: acids, such as hydrochloric acid, sulfuric acid, or hydrobromic acid; acids, such as trifluoro acetic acid, or polyphosphoric acid. Of these, polyphosphoric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 150° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours, will usually suffice.

(Step E3)

In this step, the compound (XVIa) is prepared by reduction of the carbonyl group of the compound of formula (XVa).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; sulfoxides, such as dimethyl sulfoxide and sulfolane; alcohols, such as methanol, ethanol, propanol, 2-propanol and butanol; or mixed solvents thereof. Of these, methanol or tetrahydrofuran is preferred.

The reaction is carried out in the presence of a reducing agent. There is likewise no particular restriction on the nature of the reducing agents used, and any reducing agent commonly used in reactions of this type may equally be used here. Examples of such reducing agents include: metal borohydrides, such as sodium borohydride, lithium borohydride and sodium cyanoborohydride; hydride compounds, such as lithium aluminum hydride and diisobutyl aluminum hydride. Of these, sodium borohydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 80° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 8 hours will usually suffice.

(Step E4)

In this step, the compound of formula (IIIa) is prepared by halogenation of the hydroxy group of the compound of formula (XVIa).

The reaction is normally and preferably effected in the presence or the absence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; amines, such as N-methylmorpholine, triethylamine, tripropylamine, tributylamine, diisopropylethylamine, dicyclohexylamine, N-methylpiperidine, pyridine, 4-pyrrolidinopyridine, N,N-dimethylaniline and N,N-diethylaniline; nitriles, such as acetonitrile and benzonitrile; sulfoxides, such as dimethyl sulfoxide and sulfolane; or mixed solvents thereof. Of these, diethyl ether or tetrahydrofuran is preferred.

The reaction may be carried out in the presence of a base. There is likewise no particular restriction on the nature of the bases used, and any base commonly used in reactions of this type may equally be used here. Examples of such bases include: amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, DBN, DABCO and DBU. Of these, pyridine is preferred.

The reaction is carried out in the presence of a halogenating agent. There is likewise no particular restriction on the nature of the halogenating agents used, and any halogenating agent commonly used in reactions of this type may equally be used here. Examples of such halogenating agents include: thionyl chloride, oxalyl chloride, phosphorus pentachloride and phosphorus oxychloride. Of these, thionyl chloride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 8 hours will usually suffice.

Method F

This illustrates the preparation of compounds of formula (IIIb) wherein B is $CH_2$.

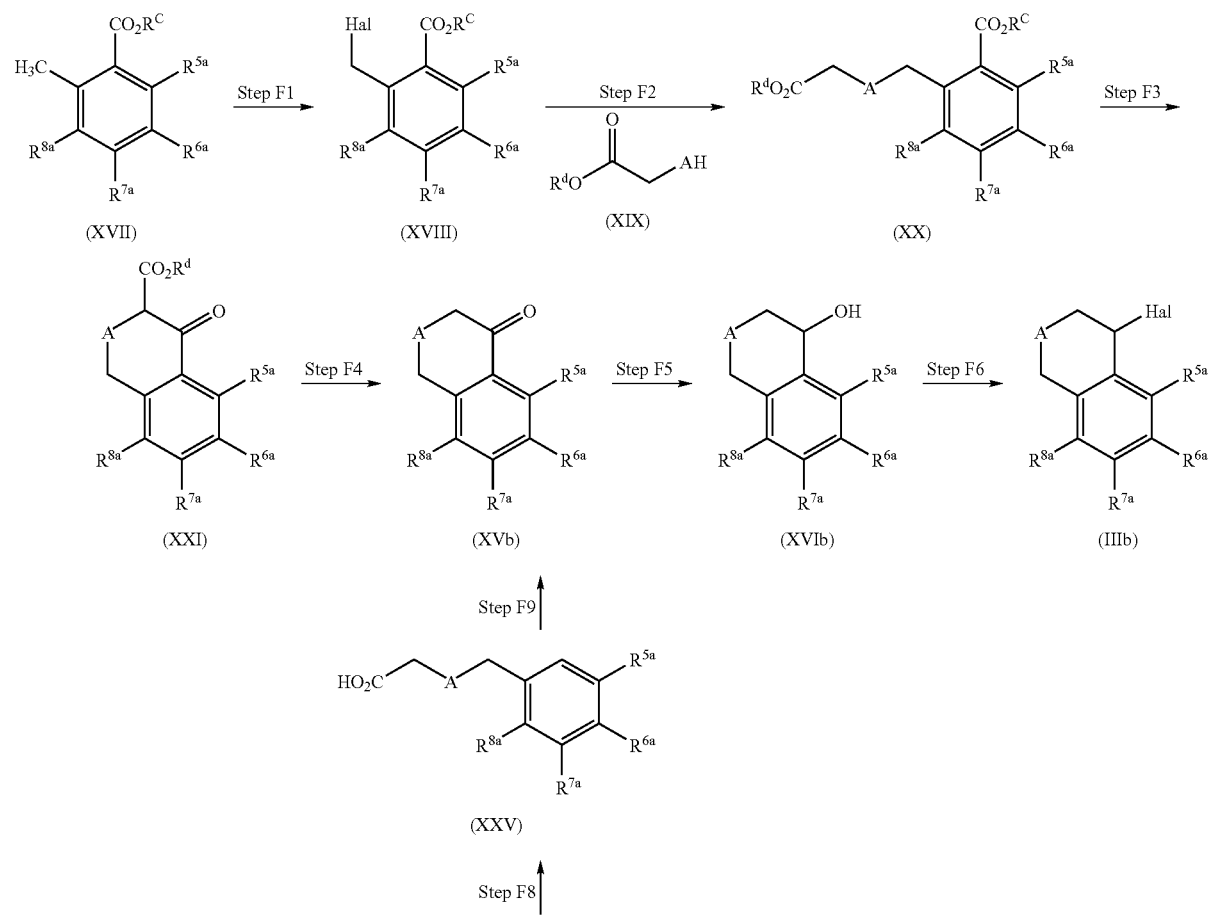

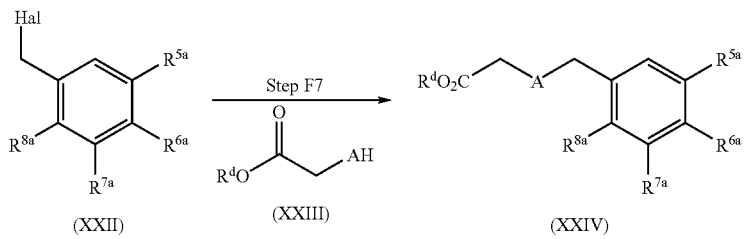

In Reaction Scheme F, $R^c$ and $R^d$ independently represent a $C_1$-$C_4$ alkyl group.

(Step F1)

In this step, the compound of formula (XVIII) is prepared by halogenation of the methyl group of the compound of formula (XVII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; nitriles, such as acetonitrile and benzonitrile; sulfoxides, such as dimethyl sulfoxide and sulfolane; or mixed solvents thereof. Of these, carbon tetrachloride or 1,2-dichloroethane is preferred.

The reaction is carried out in the presence of a halogenating agent. There is likewise no particular restriction on the nature of the halogenating agents used, and any halogenating agent commonly used in reactions of this type may equally be used here. Examples of such halogenating agents include: succinimides, such as N-bromosuccinimide (NBS), N-chlorosuccinimide (NCS); bromine. Of these, NBS is preferred.

Reagents, such as benzoyl peroxide and 2,2'-azobis(isobutyronitrile) (AIBN) may be employed for this step. Of these, benzoyl peroxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours will usually suffice.

(Step F2)

In this step, the compound of formula (XX) is prepared by ether formation reaction of the compound of formula (XVIII) with the compound of formula (XIX), which is commercially available.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; or mixed solvents thereof. Of these, N,N-dimethylformamide or tetrahydrofuran is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal hydrides, such as lithium hydride, sodium hydride and potassium hydride; alkali metal alkoxides, such as sodium methoxide, sodium ethoxide and potassium tert-butoxide; alkali metal amides, such as lithium amide, sodium amide, potassium amide, lithium diisopropyl amide, potassium diisopropyl amide, sodium diisopropyl amide, lithium bis(trimethylsilyl) amide and potassium bis(trimethylsilyl)amide. Of these, sodium hydride is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 150° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 48 hours, will usually suffice.

(Step F3)

In this step, the compound of formula (XXI) is prepared by cyclization (Dieckmann Condensation) of the compound of formula (XX).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; alcohols, such as methanol, ethanol, propanol, 2-propanol and butanol; or mixed solvents thereof. Of these, toluene is preferred.

The reaction is carried out in the presence of a base. There is likewise no particular restriction on the nature of the bases used, and any base commonly used in reactions of this type may equally be used here. Examples of such bases include: alkali metal, such as lithium and sodium; alkali metal hydrides, such as lithium hydride, sodium hydride and potassium hydride; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, sodium is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 150° C. The time required for the reaction may also vary widely, depending on many factors, notably the reaction temperature and the nature of the starting materials and solvent employed. However, provided that the reaction is effected under the preferred conditions outlined above, a period of from about 30 minutes to about 24 hours, will usually suffice.

(Step F4)

In this step, the compound of formula (XVb) is prepared by decarboxylation of the compound of formula (XXI).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; amides, such as formamide, N,N-dimethylformamide, N,N-dimethylacetamide and hexamethylphosphoric triamide; alcohols, such as methanol, ethanol, propanol, 2-propanol, ethylene glycol and butanol; nitriles, such as acetonitrile and benzonitrile; sulfoxides, such as dimethyl sulfoxide and sulfolane; water; or mixed solvents thereof. Of these, ethanol is preferred.

The reaction may be carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate. Of these, sodium hydroxide is preferred.

The reaction may be carried out in the presence of an acid. There is likewise no particular restriction on the nature of the acids used, and any acid commonly used in reactions of this type may equally be used here. Examples of such acids include: carboxylic acids, such as acetic acid or propionic acid; acids, such as hydrochloric acid, sulfuric acid, or hydrobromic acid. Of these, hydrochloric acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 20° C. to about 120° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 48 hours, will usually suffice.

(Step F5)

In this step, the compound of formula (XVIb) is prepared by reduction of the compound of formula (XVb). The reaction may be carried out under the same condition as described in Step E3 of Method E.

(Step F6)

In this step, the compound of formula (IIIb) is prepared by halogenation of the compound of formula (XVIb). The reaction may be carried out under the same condition as described in Step E4 of Method E. If the compound of formula (IIIb) has hydroxy groups, the reaction for introducing the hydroxy-protecting group described in Method E will be applied in an appropriate step.

(Step F7)

In this step, the compound of formula (XXIV) is prepared by ether formation reaction of the compound of formula (XXII) with the compound of formula (XXIII), which is commercially available. The reaction may be carried out under the same condition as described in Step F2 of Method F.

(Step F8)

In this step, the compound of formula (XXV) is prepared by hydrolysis of the compound of formula (XXIV). The reaction may be carried out under the same condition as described in Step B2 of Method B.

(Step F9)

In this step, the compound of formula (XVb) is prepared by cyclization (F9-a) of the compound of formula (XXIV) or by formation of acid halide (F9-b) followed by Friedel Crafts reaction (F9-c) of the compound of formula (XXV). The reaction may be carried out under the same condition as described in Step E2 of Method E.

Method G

This illustrates the preparation of compounds of formula (IX).

Reaction Scheme G

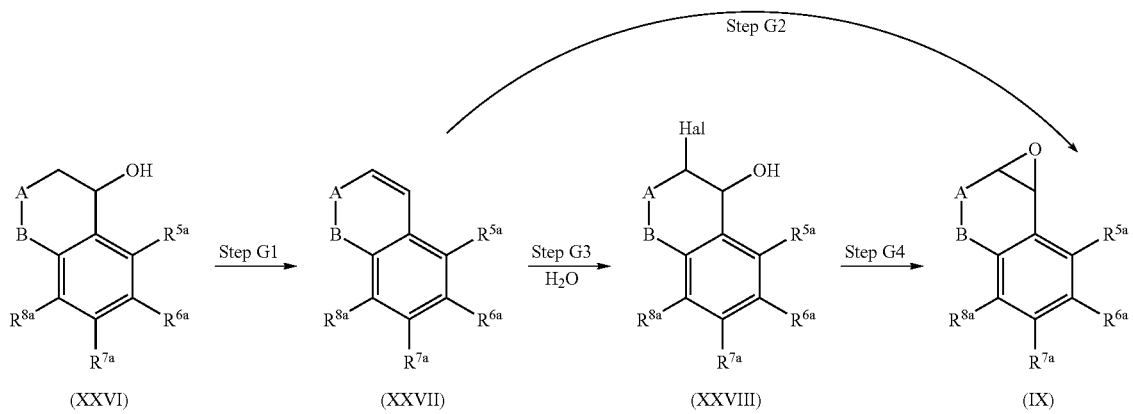

(Step G1)

In this step, the compound of formula (XXVII) is prepared by intermolecular dehydration of compound of formula (XXVI), which is commercially available or may be prepared by the foregoing method E or F.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; or mixed solvents thereof. Of these, toluene is preferred.

The reaction is carried out in the presence of an acid. There is likewise no particular restriction on the nature of the acids used, and any acid commonly used in reactions of this type may equally be used here. Examples of such acids include: carboxylic acids, such as acetic acid, trifluoro acetic acid or propionic acid; acids, such as hydrochloric acid, hydrochloric acid, sulfuric acid, or p-toluenesulfonic acid; Lewis acids, such as $BF_3$, $AlCl_3$, $FeCl_3$, $AgCl$, $ZnI_2$, $Fe(NO_3)_3$, $CF_3SO_3Si(CH_3)_3$, $Yb(CF_3SO_3)_3$ and $SnCl_4$. Of these, p-toluenesulfonic acid is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 150° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(Step G2)

In this step, the compound of formula (IX) is prepared by epoxydation of the compound of formula (XXVII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; ketones, such as acetone and diethylketone; water; or mixed solvents thereof. Of these, dichloromethane is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate; alkali metal hydrogencarbonates, such as lithium hydrogencarbonate, sodium hydrogencarbonate and potassium hydrogencarbonate; amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, DBN, DABCO and DBU. Of these, sodium hydrogencarbonate is preferred.

The reaction is carried out in the presence of an oxidizing agent. There is likewise no particular restriction on the nature of the oxidizing agents used, and any oxidizing agent commonly used in reactions of this type may equally be used here. Examples of such oxidizing agents include: peroxy acids, such as 3-chloroperbenzoic acid (MCPBA), perbenzoic acid, peracetic acid and trifluoroperacetic acid; peroxides, such as hydrogen peroxide and tert-butyl hydroperoxide. Of these, MCPBA is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about −78° C. to about 100° C. The time required for the reaction may also vary widely, depending on many factors, notably the reaction temperature and the nature of the starting materials and solvent employed. However, provided that the reaction is effected under the preferred conditions outlined above, a period of from about 10 minutes to about 24 hours, will usually suffice.

(Step G3)

In this step, the compound of formula (XXVIII) is prepared by electrophilic addition of the compound of formula (XXVII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; nitriles, such as acetonitrile and benzonitrile; sulfoxides, such as dimethyl sulfoxide and sulfolane; ketones, such as acetone and diethylketone; water; or mixed solvents thereof. Of these, dimethyl sulfoxide or water is preferred.

The reaction is carried out in the presence of a halogenating agent. There is likewise no particular restriction on the nature of the halogenating agents used, and any halogenating agent commonly used in reactions of this type may equally be used here. Examples of such halogenating agents include:succinimides, such as NBS, NCS; bromine. Of these, NBS is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 24 hours, will usually suffice.

(Step G4)

In this step, the compound of formula (IX) is prepared by epoxydation of the compound of formula (XXVIII)

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, tetrahydrofuran and dioxane; aromatic hydrocarbons, such as benzene, toluene and nitrobenzene; amides, such as formamide, N,N-dimethylformamide, N,N-dimethylacetamide and hexamethylphosphoric triamide; amines, such as N-methylmorpholine, triethylamine, tripropylamine, tributylamine, diisopropylamine, dicyclohexylamine, N-methylpiperidine, pyridine, 4-pyrrolidinopyridine, N,N-dimethylaniline and N,N-diethylaniline; alcohols, such as methanol, ethanol, propanol, 2-propanol and butanol; nitriles, such as acetonitrile and benzonitrile; sulfoxides, such as dimethyl sulfoxide and sulfolane; or mixed solvents thereof. Of these, diethyl ether is preferred.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide; alkali metal carbonates, such as lithium carbonate, sodium carbonate and potassium carbonate; alkali metal hydrogencarbonates, such as lithium hydrogencarbonate, sodium hydrogencarbonate and potassium hydrogencarbonate; amines, such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, DBN, DABCO and DBU. Of these, potassium hydroxide is preferred.

The reaction can take place over a wide range of temperatures, and the precise reaction temperature is not critical to the invention. The preferred reaction temperature will depend upon such factors as the nature of the solvent, and the starting materials. However, in general, it is convenient to carry out the reaction at a temperature of from about 0° C. to about 100° C. The time required for the reaction may also vary widely, depending on many factors, notably the reaction temperature and the nature of the starting materials and solvent employed. However, provided that the reaction is effected under the preferred conditions outlined above, a period of from about 60 minutes to about 48 hours, will usually suffice.

The compounds of formula (I), and the intermediates in the above-mentioned preparation methods can be isolated and purified by conventional procedures, such as distillation, recrystallization or chromatographic purification.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

Alternatively, a method of optical resolution of a racemate (or a racemic precursor) can be appropriately selected from conventional procedures, for example, preferential crystallization, or resolution of diastereomeric salts between a basic moiety of the compound of formula (I) and a suitable optically active acid such as tartaric acid.

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a pharmaceutical composition or formulation in association with one or more pharmaceutically acceptable carriers or excipients.

The term "carrier" or "excipient" is used herein to describe any ingredient other than the compound(s) of the invention. The choice of carrier or excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface-active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "*Pharmaceutical Dosage Forms: Tablets, Vol. 1*", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, *Pharmaceutical Technology On-line*, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from about 3 to about 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci,* 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from about 1 µg to about 20 mg of the compound of the invention per actuation and the actuation volume may vary from about 1 µl to about 100 µl. Atypical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration. Formulations for inhaled/intranasal administration may be formulated to be immediate and/or modified release using, for example, poly(DL-lactic-coglycolic acid) (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from about 1 to about 100 µg of the compound of formula (I). The overall daily dose will typically be in the range about 50 µg to about 20 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in. WO 91/11172, WO 94/02518 and WO 98/55148.

Kit-Of-Parts

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range of about 0.05 mg to about 100 mg depending, of course, on the mode of administration, preferred in the range of about 0.1 mg to about 50 mg and more preferred in the range of about 0.5 mg to about 20 mg. For example, oral administration may require a total daily dose of from about 1 mg to about 20 mg, while an intravenous dose may only require from about 0.5 mg to about 10 mg. The total daily dose may be administered in single or divided doses.

These dosages are based on an average human subject having a weight of about 65 kg to about 70 kg. The physician will readily be able to determine doses for subjects whose weight falls outside this range, such as infants and the elderly.

An acid pump antagonist of the present invention may be usefully combined with another pharmacologically active compound, or with two or more other pharmacologically active compounds, particularly in the treatment of gastroesophageal reflux disease. For example, an acid pump antagonist, particularly a compound of the formula (I), or a pharmaceutically acceptable salt thereof, as defined above, may be administered simultaneously, sequentially or separately in combination with one or more agents selected from:

(i) histamine $H_2$ receptor antagonists, e.g. ranitidine, lafutidine, nizatidine, cimetidine, famotidine and roxatidine;

(ii) proton pump inhibitors, e.g. omeprazole, esomeprazole, pantoprazole, rabeprazole, tenatoprazole, ilaprazole and lansoprazole;

(iii) oral antacid mixtures, e.g. Maalox®, Aludrox® and Gaviscon®;

(iv) mucosal protective agents, e.g. polaprezinc, ecabet sodium, rebamipide, teprenone, cetraxate, sucralfate, chloropylline-copper and plaunotol;

(v) anti-gastric agents, e.g. Anti-gastrin vaccine, itriglumide and Z-360;

(vi) 5-$HT_3$ antagonists, e.g. dolasetron, palonosetron, alosetron, azasetron, ramosetron, mitrazapine, granisetron, tropisetron, E-3620, ondansetron and indisetron;

(vii) 5-$HT_4$ agonists, e.g. tegaserod, mosapride, cinitapride and oxtriptane;

(viii) laxatives, e.g. Trifyba®, Fybogel®, Konsyl®, Isogel®, Regulan®, Celevac® and Normacol®;

(ix) $GABA_B$ agonists, e.g. baclofen and AZD-3355;

(x) $GABA_B$ antagonists, e.g. GAS-360 and SGS-742;

(xi) calcium channel blockers, e.g. aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xii) dopamine antagonists, e.g. metoclopramide, domperidone and levosulpiride;

(xiii) Tachykinin (NK) antagonists, particularly NK-3, NK-2 and NK-1 antagonists, e.g.: nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[(2R,3S)-2-[(1R)-1-[3,5-bis(trifluoromethyl)phenyl]ethoxy-3-(4-fluoropheny)-4-morpholinyl]methyl]-1,2-dihydro-3 H-1,2,4-triazol-3-one (MK-869), lanepitant, dapitant and 3-[[2-methoxy-5-(trifluoromethoxy)phenyl]methylamino]-2-phenyl-piperidine (2S,3S);

(xiv) *Helicobacter pylori* infection agents, e.g., clarithromicyn, roxithromycin, rokitamycin, flurithromycin, telithromycin, amoxicillin, ampicillin, temocillin, bacampicillin, aspoxicillin, sultamicillin, piperacillin, lenampicillin, tetracycline, metronidazole, bithmuth citrate and bithmuth subsalicylate.

(xv) nitric oxide synthase inhibitors, e.g. GW-274150, tilarginine, P54, guanidioethyldisulfide and nitroflurbiprofen;

(xvi) vanilloid receptor 1 antagonists, e.g. AMG-517 and GW-705498;

(xvii) muscarinic receptor antagonists, e.g. trospium, solifenacin, tolterodine, tiotropium, cimetropium, oxitropium, ipratropium, tiquizium, dalifenacin and imidafenacin;

(xviii) calmodulin antagonists, e.g. squalamine and DY-9760;

(xix) potassium channel agonists, e.g. pinacidil, tilisolol, nicorandil, NS-8 and retigabine;

(xx) beta-1 agonists, e.g. dobutamine, denopamine, xamoterol, denopamine, docarpamine and xamoterol;

(xxi) beta-2 agonists, e.g. salbutamol; terbutaline, arformoterol, meluadrine, mabuterol, ritodrine, fenoterol, clenbuterol, formoterol, procaterol, tulobuterol, pirbuterol, bambuterol, tulobuterol, dopexamine and levosalbutamol;

(xxii) beta agonists, e.g. isoproterenol and terbutaline;

(xxiii) alpha 2 agonists, e.g. clonidine, medetomidine, lofexidine, moxonidine, tizanidine, guanfacine, guanabenz, talipexole and dexmedetomidine;

(xxiv) endthelin A antagonists, e.g. bonsetan, atrasentan, ambrisentan, clazosentan, sitaxsentan, fandosentan and darusentan;

(xxv) opioid μ agonists, e.g. morphine, fentanyl and loperamide;

(xxvi) opioid μ antagonists, e.g. naloxone, buprenorphine and alvimopan;

(xxvii) motilin agonists, e.g. erythromycin, mitemcinal, SLV-305 and atilmotin;

(xxviii) ghrelin agonists, e.g. capromorelin and TZP-101;

(xxix) AchE release stimulants, e.g. Z-338 and KW-5092;

(xxx) CCK-B antagonists, e.g. itriglumide, YF-476 and S-0509;

(xxxi) glucagon antagonists, e.g. NN-2501 and A-770077.

Method for Assessing Biological Activities:

The acid pump inhibitory activity and other biological activities of the compounds of this invention were determined by the following procedures Preparation of Gastric Vesicles from Fresh Porcine Stomachs The porcine gastric vesicles for Porcine gastric $H^+/K^+$-ATPase inhibition assays were prepared from mucous membrane in fresh porcine stomachs by homogenization with a tight-fitted polytetrafluoroethylene (Teflone®) homogenizer in 0.25 M sucrose at 4° C. The crude pellet was removed with centrifugation at 20,000 g for 30 min. Then supernatant was centrifuged at 100,000 g for 30 min. The resulting pellet was re-suspended in 0.25 M sucrose, and then subjected to density gradient centrifugation at 132,000 g for 90 min. The gastric vesicles were collected from interface on 0.25 M sucrose layer containing 7% Ficoll™ PM400(Amersham Biosciences). This procedure was performed in a cold room.

Ion-Leaky Porcine Gastric H+/K+-ATPase Inhibition

Ion-leaky porcine gastric $H^+/K^+$-ATPase_inhibition was measured according to the modified method described in *Biochemical Pharmacology,* 1988, 37, 2231-2236.

The isolated vesicles were lyophilized, and then kept in deep-freezer until use. For enzyme assay, lyophilized vesicles were reconstituted with 3 mM $MgSO_4$ containing 40 mM Bis-tris (pH 6.4 at 37° C.).

Enzyme reaction was performed incubating 5 mM KCl, 3 mM $Na_2ATP$, 3 mM $MgSO_4$ and 1.0 µg of reconstituted vesicles for 30 minutes at 37° C. in a final 60 µl of reaction mixture (40 mM Bis-tris, pH 6.4) with or without the test compound. Enzyme reaction was stopped by adding 10% sodium dodecyl sulphate (SDS). Released inorganic phosphate from ATP was detected by incubation with mixture of 1 part of 35 mM ammonium molybdate tetrahydrate in 15 mM Zinc acetate hydrate and 4 parts of 10% ascorbic acid (pH 5.0), resulting in phosphomolybdate, which has optical density at 750 nm. All example compounds showed potent inhibitory activity.

Ion-tight Porcine Gastric H+/K+-ATPase Inhibition

Ion-tight porcine gastric $H^+/K^+$-ATPase inhibition was measured according to the modified method described in *Biochemical Pharmacology,* 1988, 37, 2231-2236.

The isolated vesicles were kept in deep-freezer until use. For enzyme assay, vesicles were diluted with 3 mM $MgSO_4$ containing 5 mM Tris (pH 7.4 at 37° C).

Enzyme reaction was performed incubating 150 mM KCl, 3 mM $Na_2ATP$, 3 mM $MgSO_4$, 15 µM valinomycin and 3.0 µg of vesicles for 30 minutes at 37° C. in a final 60 µl of reaction mixture (5 mM Tris, pH 7.4) with or without the test compound. Enzyme reaction was stopped by adding 10% SDS. Released inorganic phosphate from ATP was detected by incubating with mixture of 1 part of 35 mM ammonium molybdate tetrahydrate in 15 mM Zinc acetate hydrate and 4 parts of 10% ascorbic acid (pH 5.0), resulting in phosphomolybdate, which has optical density at 750 nm.

The results of $IC_{50}$ values of the inhibitory activity for the compounds of following examples are shown in Table 1.

TABLE 1

| Example No. | $IC_{50}$ (µM) |
|---|---|
| 1 | 0.56 |
| 2 | 0.069 |
| 3 | 0.44 |
| 4 | 0.44 |
| 5 | 0.090 |
| 6 | 0.21 |
| 7 | 0.22 |
| 8 | 0.18 |
| 9 | 0.96 |
| 10 | 0.32 |

TABLE 1-continued

| Example No. | $IC_{50}$ (µM) |
|---|---|
| 11 | 0.43 |
| 12 | 0.67 |
| 13 | 0.12 |
| 14 | 0.98 |
| 15 | 0.95 |
| 16 | 0.14 |
| 17 | 0.34 |
| 18 | 0.24 |
| 19 | 0.68 |
| 20 | 0.61 |
| 21 | 0.49 |
| 22 | 0.18 |
| 23 | 0.44 |
| 24 | 0.62 |
| 25 | 0.59 |
| 26 | 0.48 |

All the tested compounds showed acid pump antagonistic activity.

Canine Kidney $Na^+/K^+$-ATPase Inhibition

The powdered canine kidney $Na^+/K^+$-ATPase (Sigma) was reconstituted with 3 mM $MgSO_4$ containing 40 mM Tris (pH 7.4 at 37° C.). Enzyme reaction was performed incubating 100 mM NaCl, 2 mM KCl, 3 mM $Na_2ATP$, 3 mM $MgSO_4$ and 12 µg of enzyme for 30 minutes at 37° C. in a final 60 µl of reaction mixture (40 mM Tris, pH 7.4) with or without the test compound. Enzyme reaction was stopped by adding 10% SDS. Released inorganic phosphate from ATP was detected by incubating with mixture of 1 part of 35 mM ammonium molybdate tetrahydrate in 15 mM Zinc acetate hydrate and 4 parts of 10% ascorbic acid (pH 5.0), resulting in phosphomolybdate, which has optical density at 750 nm.

Inhibition of Acid Secretion in the Gastric Lumen-Perfused Rat

Acid secretion in the gastric lumen-perfused rat was measured according to Watanabe et al. [Watanabe K et al., *J. Physiol.* (Paris) 2000; 94: 111-116].

Male Sprague-Dawley rats, 8 weeks old, deprived of food for 18 hours before the experiment with free access to water, were anesthetized with urethane (1.4 g/kg, i.p.) and tracheotomized. After a middle abdominal incision, a dual polyethylene cannula was inserted into the forestomach and the stomach was perfused with saline (37° C., pH 5.0) at a rate of 1 ml/min. The acid output in the perfusate was determined at 5 minutes interval by titration with 0.02 N NaOH to pH 5.0. After the determination of basal acid secretion for 30 min, the acid secretion was stimulated by a continuous intravenous infusion of pentagastrin (16 µg/kg/h). The test compounds were administered by an intravenous bolus injection or intraduodenal administration after the stimulated acid secretion reached a plateau phase. The acid secretion was monitored after the administration.

The activity was evaluated either inhibition of total acid secretion from 0 hours to 1.5 or 3.5 hours after administration or the maximum inhibition after administration.

Inhibition of Gastric Acid Secretion in the Heidenhain Pouch Dog

Male Beagle dogs weighing 7-15 kg with Heidenhain pouch [Heidenhain R: *Arch Ges Physiol.* 1879; 19: 148-167] were used. The animals were allowed to recover from surgery for at least three weeks before the experiments. The animals were kept at a 12 hour light-dark rhythm, housed singly. They received standard food once daily at 11:00 a.m. and tap water ad libitum, and were fasted overnight prior to the experiment, with free access to water. Gastric juice samples were collected throughout the experiment by gravity drainage every 15 min. Acidity in the gastric juice was measured by titration to the end point of pH 7.0. Acid secretion was stimulated by a continuous intravenous infusion of histamine (80 μg/kg/h). Oral or intravenous bolus administration of the test compounds was done 90 minutes after commencement of the histamine infusion. The acid secretion was monitored after the administration. The activity was evaluated by the maximum inhibition relative to the corresponding control value.

The compound of Example 6 showed a good inhibitory activity.

Human Dofetilide Binding

Human ether a-go-go related gene (HERG) transfected HEK293S cells were prepared and grown in-house. Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit (wako) and Spectra max plate reader (Wallac). All the manipulation, stock solution and equipment were kept on ice at all times. For saturation assays, experiments were conducted in a total volume of 200 μl. Saturation was determined by incubating 36 μl of [$^3$H]-dofetilide, and 160 μl of membrane homogenates (20-30 μg protein per well) for 60 minutes at room temperature in the absence or presence of 10 μM dofetilide at final concentrations (4 μl) for total or nonspecific binding, respectively. All incubations were terminated by rapid vacuum filtration over PEI soaked glass fiber filter papers using Skatron cell harvester followed by two washes with 50 mM Tris buffer (pH 7.4 at 25° C). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.4 at 25° C.) containing 1 mM $MgCl_2$, 10 mM KCl so that the final DMSO concentration became equal to 1%. Compounds were dispensed in triplicate in assay plates (4 μl). Total binding and nonspecific binding wells were set up in 6 wells as vehicle and 10 μM dofetilide at final concentration, respectively. The radioligand was prepared at 5.6× final concentration and this solution was added to each well (36 μl). The assay was initiated by addition of YSi poly-L-lysine SPA beads (50 μl, 1 mg/well) and membranes (110 μl, 20 μg/well). Incubation was continued for 60 minutes at room temperature. Plates were incubated for a further 3 hours at room temperature for beads to settle. Receptor-bound radioactivity was quantified by counting Wallac MicroBeta plate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM 2-morpholinoethanesulphonic acid (MES) Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM 2-[4-(2-hydroxyethyl)-1-piperazinyl]ethanesulfonic acid (HEPES) Biological Buffer, 1.25 mM $CaCl_2$ and 0.5 mM $MgCl_2$ (pH 7.4). At the end of the preincubation, the media was removed and test compound solution (10 μM) in buffer was added to the apical compartment. The inserts were moved to wells containing fresh basolateral buffer at 1 hour. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app}(cm/sec)=(F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity was determined by Lucifer Yellow transport.

Half-life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 minutes time point, where 0 minutes time point indicated the time when NADPH was added into the reaction mixture of P450 group. An aliquot of samples of non-P450 group was collected at −10 and 65 minutes time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

$$Half\text{-}life = \ln 2/k$$

In vitro Drug-Drug Interaction Studies for Five Major CYPs (fDDI)

CYP1A2 Test compounds (3 μM) were pre-incubated with recombinant CYP1A2 (Baculosome lot #21198 Invitrogen, 50 pmol P450/ml) in 100 mM K$^+$Phosphate Buffer (pH 7.4) and 10 μM Vivid blue 1A2 probe (Invitrogen) as a substrate for 5 minutes at 30° C. Reaction was initiated by adding a solution of a warmed NADPH-regenerating system A, which consists of 0.50 mM NADP and 10 mM $MgCl_2$, 6.2 mM DL-Isocitric acid and 0.5 U/ml Isocitric Dehydrogenase (ICD). Plates were placed in the plate reader at 30° C. and were taken readings every 1.5 minutes, with a 10 second shake in between each reading for 15 cycles. Wavelengths of excitation/emission were 408/465 nm, respectively.

CYP2C9 Test compounds (3 μM) were pre-incubated with recombinant CYP2C9 (Baculosome lot #20967 Invitrogen, 50 pmol P450/ml) in 100 mM K+Phosphate Buffer (pH 7.4) and 30 μM MFC probe (Gentest) as a substrate for 5 minutes at 37° C. Reaction was initiated by adding a solution of the warmed NADPH-regenerating system A. Plates were placed in the plate reader at 37° C. and were taken readings every 2.0 minutes, with a 10 second shake in between each reading for 15 cycles. Wavelengths of excitation/emission were 408/535 nm, respectively.

CYP2C19 Test compounds (3 μM) were pre-incubated with recombinant CYP2C19 (Baculosome lot #20795 Invitrogen, 5 pmol P450/ml) in 100 mM K+Phosphate Buffer (pH 7.4) and 10 μM Vivid blue 2C19 probe (Invitrogen) as a substrate for 5 minutes at 37° C. Reaction was initiated by adding a solution of the warmed NADPH-regenerating system A. Plates were placed in the plate reader at 37° C. and were taken readings every 1.5 minutes with a 10 second shake in between each reading for 15 cycles. Wavelengths of excitation/emission were 408/465 nm, respectively.

CYP2D6 Test compounds (3 μM) were pre-incubated with recombinant CYP2D6 (Baculosome lot #21248 Invitrogen, 20 pmol P450/ml) in 100 mM K+Phosphate Buffer (pH 7.4) and 1 μM 3-[2-(N,N-diethyl-N-methylammonium)ethyl]-7-methoxy-4-methylcoumarin (AMMC) probe (Gentest) as a substrate for 5 minutes at 37° C. Reaction was initiated by adding a solution of a warmed NADPH-regenerating system B, which consists of 0.03 mM NADP and 10 mM $MgCl_2$, 6.2 mM DL-Isocitric acid and 0.5 U/ml ICD. Plates were placed in the plate reader at 37° C. and were taken readings every 2.0 minutes with a 10 second shake in between each reading for 15 cycles. Wavelengths of excitation/emission were 400/465 nm, respectively.

CYP3A4 Test compounds (3 μM) were pre-incubated with recombinant CYP3A4 (Baculosome lot #20814 Invitrogen, 5 pmol P450/ml) in 100 mM K+Phosphate Buffer (pH 7.4) and 2 μM Vivid Red probe (Invitrogen) as a substrate for 5 minutes at 30° C. Reaction was initiated by adding a solution of the warmed NADPH-regenerating system A. Plates were placed in the plate reader at 30° C. and were taken readings minimum intervals with a 10 second shake in between each reading for 15 cycles. Wavelengths of excitation/emission were 530/595 nm, respectively.

Drug-drug interaction was evaluated by the rate of metabolite formation calculated with a slope (Time vs. Fluorescence units) in the linear region or the percentage of inhibition by test compounds calculated by the following equation.

Inhibition %={$(v_o-v_i)/v_o$}*100, wherein $v_o$ is a rate of control reaction (no test compounds) and $v_i$ is a rate of reaction in the presence of test compound.

$I_{HERG}$ Assay

Human ether a-go-go related gene (HERG) transfected HEK293 cells are prepared and cultured in-house. The methodology for stable transfection of this channel in HEK cells can be found elsewhere (Z.Zhou et al., 1998, *Biophysical journal*, 74, 230-241). On the day of experimentation, the cells are harvested from culture flasks and stored as cell suspension in a standard external solution (see below of its composition). in the room atmosphere of 23° C. Cells are studied between 0.5-5 hours after harvest.

HERG currents are studied using a standard patch clamp technique of the whole-cell mode. During the experiment, the cells are superfused with a standard external solution of the following composition;(mM) NaCl, 130; KCl, 4; $CaCl_2$, 2; $MgCl_2$, 1; Glucose, 10; HEPES, 5; pH 7.4 with NaOH. Whole-cell recordings is made using a patch clamp amplifier and patch pipettes which have a resistance of 1-3 MOhm when filled with the standard internal solution of the following composition; (mM); KCl, 130; MgATP, 5; $MgCl_2$, 1; HEPES, 10; EGTA 5, pH 7.2 with KOH. Only those cells with access resistances below 10 MOhm and seal resistances over 1 GOhm are accepted for further experimentation. Series resistance compensation is applied up to a maximum of 80% without any leak subtraction. Following the achievement of whole cell configuration and sufficient time for cell dialysis with pipette solution (>5 min), the membrane is depolarized from a holding potential of −80 mV to +30 mV for 1000 ms followed by a descending voltage ramp (rate 0.5 mV msec$^{-1}$) back to the holding potential. This depolarization and ramp is applied to the cells continuously every 4 seconds (0.25 Hz). The amplitude of the peak current elicited around −40 mV during the ramp is measured. Once stable evoked current responses of minimal changes in the amplitude are obtained in the external solution, the test compound is applied for 10-20 minutes with multiple dosing in a single cell. The cells are also exposed to high dose of dofetilide (5 μM), a specific IKr blocker, to evaluate the insensitive endogenous current.

All experiments are performed at 23+/−1° C. Evoked membrane currents are recorded online on a computer, filtered at 500-1000 Hz (Bessel −3 dB) and sampled at 1-2 KHz. Osmolarity and pH change induced by the test compound in external solution will be examined at the highest concentration.

The arithmetic mean of these ten values of peak current is calculated under control conditions and in the presence of drug. Percent decrease of $I_N$ in each experiment is obtained by the normalized current value using the following formula: $I_N=(I_C-I_D)/(I_C-I_{dof})\times 100$, where $I_c$ is the mean current value under control conditions, $I_D$ is the mean current value in the presence of test compound and $I_{dof}$ is the mean current value in dofetilide application. Separate experiments are performed and pooled data of arithmetic mean from each experiment is defined as the result of the study.

hERG Patch Clamp Assay

To determine the potential of compounds to inhibit the hERG channel, the cloned counterpart of the rapidly inactivating delayed rectifier potassium current (IKr).

HEK293 cells stably expressing the hERG channel were used in whole-cell patch clamp electrophysiology studies at ambient temperature (26.5-28.5° C.). The methodology for stable transfection of this channel in HEK293 cells can be found elsewhere (Zhou et al 1998, Biophysical Journal, 74, pp230-241). The solutions used for experimentation were standard extracellular solution of the following composition (mM); NaCl, 137; KCl, 4; $CaCl_2$, 1.8; $MgCl_2$, 1; Glucose, 10; HEPES, 10; pH 7.4±0.05 with NaOH/HCl; and standard intracellular solution of the following composition (mM); KCl, 130; $MgCl_2$, 1; HEPES, 10; EGTA, 5; MgATP, 5; pH 7.2±0.05 with KOH. The voltage protocol applied was designed to activate the hERG channel and allow the measurement of drug block of the channel and is as follows. First the membrane potential was stepped from a holding potential of −80 mV to +30 mV for 1 s. This was followed by a descending voltage ramp at a rate of 0.5 mV/ms back to holding potential of −80 mV and the peak outward current observed during the repolarizing ramp was measured. This protocol was evoked repeatedly every 4 seconds (0.25 Hz). After establishing a stable baseline period in the presence of vehicle (0.1% v/v DMSO), four increasing concentrations of test compound were then bath-applied sequentially until the response reached steady-state or 10 minutes (whichever occurred first). 10 micromol/L dofetilide was used at the end of each experiment as an internal positive control and to define maximum block.

Bioavailability in Rat

Adult rats of the Sprague-Dawley strain were used. One to two days prior to the experiments all rats were prepared by cannulation of the right jugular vein under anesthesia. The cannula was exteriorized at the nape of the neck. Blood samples (0.2-0.3 mL) were drawn from the jugular vein at intervals up to 24 hours after intravenous or oral administrations of the test compound. The samples were frozen until analysis. Bioavailability was assessed by calculating the quotient between the area under plasma concentration curve (AUC) following oral administration or intravenous administration.

Bioavailability in Dog

Adult Beagle dogs were used. Blood samples (0.2-0.5 mL) were drawn from the cephalic vein at intervals up to 24 hours after intravenous or oral administrations of the test compound. The samples were frozen until analysis. Bioavailability was assessed by calculating the quotient between the area under plasma concentration curve (AUC) following oral administration or intravenous administration.

Plasma Protein Binding

Plasma protein binding of the test compound (1 μM) was measured by the method of equilibrium dialysis using 96-well plate type equipment. Spectra-Por®, regenerated cellulose membranes (molecular weight cut-off 12,000-14,000, 22 mm×120 mm) were soaked for over night in distilled water, then for 20 minutes in 30% ethanol, and finally for 15 minutes in dialysis buffer (Dulbecco's phosphate buffered saline, pH 7.4). Frozen plasma of human, Sprague-Dawley rats, and Beagle dogs were used. The dialysis equipment was assembled and added 150 μL of compound-fortified plasma to one side of each well and 150 μL of dialysis buffer to the other side of each well. After 4 hours incubation at 37° C. for 150 r.p.m, aliquots of plasma and buffer were sampled. The compound in plasma and buffer were extracted with 300 μL of acetonitrile containing internal standard compounds for analysis. The concentration of the compound was determined with LC/MS/MS analysis.

The fraction of the compound unbound was calculated by the following equation:

$$fu = 1 - \{([plasma]_{eq} - [buffer]_{eq})/([plasma]_{eq})\}$$

wherein $[plasma]_{eq}$ and $[buffer]_{eq}$ are the concentrations of the compound in plasma and buffer, respectively.

Aqueous Solubility

Aqueous solubility in the mediums (a)-(c) was determined by following method:

Whatman mini-UniPrep chambers (Clifton, N.J., USA) containing more than 0.5 mg of compound and 0.5 mL of each medium were shaken overnight (over 8 hours) at room temperature. All samples were filtered through a 0.45 μm Polyvinylidene Difluoride (PVDF) membrane into the Whatman mini-UniPrep plunger before analysis. The filtrates were assayed by HPLC.

<medium>(a) Simulated gastric fluid with no enzyme (SGN) at pH 1.2: Dissolve 2.0 g of NaCl in 7.0 mL of 10 N HCl and sufficient water to make 1000 mL; (b) Phosphate buffer saline (PBS) at pH 6.5: Dissolve 6.35 g of $KH_2PO_4$, 2.84 g of $Na_2HPO_4$ and 5.50 g of NaCl in sufficient water to make 1000 mL, adjusting the pH to 6.5; (c) 3.94 mg of sodium taurocholate (NaTC) and 1.06 mg of 1-palmitoyl-2-oleyl-L-phosphatidylcholine (POPC) in 1 mL of PBS (pH 6.5).

Estimation of Hepatic Clearance Using the Metabolic Stability in Human Hepatocytes Tested compounds (1 μM) were incubated statically with hepatocytes from human at 37° C. in a 95% air/5% $CO_2$ with target cell density of $0.5 \times 10^6$ cells/ml and a total volume of 50 μL. Incubation was stopped at each time point by the addition of ice-cold acetonitrile (ACN). Aliquots of samples were mixed with 10% ACN containing an internal standard for LC/MS/MS analysis. After samples were sonicated for 10 minutes, samples were centrifuged at 2,000 rpm for 15 minutes, and then the supernatant was transferred to the other plates for analysis. The compound concentrations in supernatant were measured by LC/MS/MS system.

The disappearance rates of tested compounds were obtained by plotting the common logarithm of the peak area ratio of compounds/internal standard versus time. The slope of the line of best fit through the points yielded the rate of metabolism ($k_e$). This value was scaled to take hepatocellularity, liver and body weight into account to give an intrinsic clearance value ($CL_{int}$) in ml/min/kg as illustrated in Equation 1. Hepatic clearance ($CL_h$) was predicted from this intrinsic clearance value using the parallel tube model as shown in Equation 2. The predicted clearance divided by the hepatic blood flow ($Q_h$) afforded the extraction ratio ($E_h$) (Equation 3).

$$k_e \times (\text{g liver/kg body weight}) \times (\text{ml incubation/number of cells in incubation}) \times (\text{cells/g liver}) \qquad \text{Equation 1:}$$

$$CL_h = Q_h \times \{1 - \exp(-CL_{int}/Q_h)\} \qquad \text{Equation 2:}$$

$$E_h = CL_h/Q_h \qquad \text{Equation 3:}$$

Wherein, "gliver weight/kg body weight" is 21, "Cells/g liver" is $1.2 \times 10^8$, "ml incubation/number of cells in incubation" is $2.0 \times 10^{-6}$, and $Q_h$ is 20 ml/min/kg.

Supposing that hepatic metabolism is the main route of drug elimination, systemic exposure ($AUC_{po}$) after oral administration is calculated using Equation 4.

$$AUC_{po} = \text{Dose} \times (1 - E_h)/CL_h \qquad \text{Equation 4}$$

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates or Merck $NH_2$ gel (an amine coated silica gel) $F_{254s}$ precoated TLC plates), mass spectrometry, nuclear magnetic resonance spectra (NMR), infrared absorption spectra (IR) or microanalysis. Yields are given for illustrative purposes only. Workup with a cation-exchange column was carried out using SCX cartridge (Varian Bond-Elute), which was preconditioned with methanol. Flash column chromatography was carried out using Merck silica gel 60 (63-200 μm), Wako silica gel 300HG (40-60 μm), Fuji Silysia NH gel (an amine coated silica gel) (30-50 μm), Biotage KP-SIL (32-63 μm) or Biotage AMINOSILICA (an amine coated silica gel) (40-75 μm). Preparative TLC was carried out using Merck silica gel 60 $F_{254}$ precoated TLC plates (0.5 or 1.0 mm thickness). Low-resolution mass spectral data (EI) were obtained on an Integrity (Waters) mass spectrometer. Low-resolution mass spectral data (ESI) were obtained on ZMD™ or ZQ™ (Waters) and mass spectrometer. NMR data were determined at 270 MHz (JEOL JNM-LA 270 spectrometer), 300 MHz (JEOL JNM-LA300 spectrometer) or 600 MHz (Bruker AVANCE 600 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br s=broad singlet, etc. IR spectra were measured by a Fourier transform infrared spectrophotometer (Shimazu FTIR-8300). Optical rotations were measured using a JASCO DIP-370 Digital Polarimeter (Japan Spectroscopic CO, Ltd.). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield), mm (millimeter(s)), min (minute(s)).

Example 1

4-(3,4-Dihydro-2H-chromen-4-yloxy)-N,N,1,2-tetramethyl-1H-benzimidazole-6-carboxamide

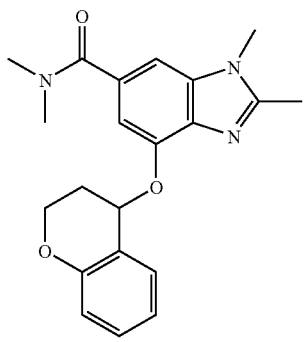

To a stirred suspension of 4-hydroxy-N,N,1,2-tetramethyl-1H-benzimidazole-6-carboxamide (50 mg, 0.21 mmol, WO 2004054984) in N,N-dimethylformamide (2 mL) was added sodium hydride (60% dispersion in mineral oil, 11 mg, 0.27 mmol) at room temperature. After stirring for 20 minutes, a solution of 4-chlorochromane (71 mg, 0.42 mmol, WO 2000078751) in N,N-dimethylformamide (1 mL) was added at room temperature. The reaction mixture was warmed to 70° C., and stirred for 6 hours at the same temperature. The reaction mixture was quenched with sodium hydrogencarbonate aqueous solution, and extracted with ethyl acetate (20 mL×2). The combined extracts were washed with water and brine, dried over magnesium sulfate, and concentrated in vacuum. The residue was purified by column chromatography on silica gel (ethyl acetate:methanol=10:1 as an eluent) to afford the title compound as a white solid (40 mg, 52%):
$^1$H NMR (CDCl$_3$) δ: 7.34-7.27 (m, 1H), 7.25-7.16 (m, 1H), 7.11 (s, 1H), 6.91-6.80 (m, 3H), 5.99 (t, J=3.3 Hz, 1H), 4.52-4.40 (m, 1H), 4.32-4.22 (m, 1H), 3.73 (s, 3H), 3.20-2.90 (m, 6H), 2.62 (s, 3H), 2.43-2.13 (m, 2H) ppm;
MS (ESI): 366 (M+H)$^+$, 364 (M−H)$^−$.

Example 2

4-[(7-Fluoro-3,4-dihydro-2H-chromen-4-yl)oxy]-N,N,1,2-tetramethyl-1H-benzimidazole-6-carboxamide

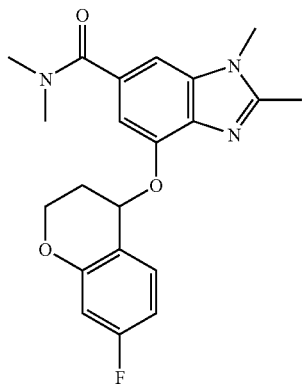

Step 1: 7-Fluorochroman-4-ol

To a solution of 7-fluoro-2,3-dihydro-4H-chromen-4-one (6.25 g, 37.6 mmol, US 20050038032) in methanol (60 mL) was added sodium borohydride (1.57 g, 41.4 mmol) at 0° C. The reaction mixture was stirred at the same temperature for 1 hour, and evaporated to remove methanol. The residue was quenched with water, and extracted with ethyl acetate. The extract was washed with brine, dried over magnesium sulfate, and concentrated in vacuum. The residue was purified by column chromatography on silica gel (hexane:ethyl acetate=3:1 as an eluent) to afford the title compound as a pale gray solid (4.70 g, 74%):
$^1$H NMR (CDCl$_3$) δ: 7.35-7.22 (m, 1H), 6.70-6.50 (m, 2H), 4.83-4.72 (m, 1H), 4.27 (dd, J=7.3, 3.7 Hz, 2H), 2.18-1.90 (m, 3H) ppm.

Step 2: 4-Chloro-7-fluorochromane

To a solution of 7-fluorochroman-4-ol (1.80 g, 10.7 mmol, STEP 1) and pyridine (0.35 mL) in diethyl ether (14 mL) was added thionyl chloride (3.9 mL, 53.5 mmol) at 0° C. The reaction mixture was stirred at the same temperature for 3 hours, and evaporated to remove excess thionyl chloride. The residue was quenched with water, and extracted with ethyl acetate. The extract was washed with brine, dried over magnesium sulfate, and concentrated in vacuum to afford the title compound as a pale brown solid (2.0 g, quant.):
$^1$H NMR (CDCl$_3$) δ: 7.24 (dd, J=8.6, 5.9 Hz, 1H), 6.68-6.58 (m, 1H), 6.53 (dd, J=9.9, 2.6 Hz, 1H), 5.25-5.18 (m, 1H), 4.56-4.28 (m, 2H), 2.55-2.39 (m, 1H), 2.34-2.24 (m, 1H) ppm.

Step 3: 4-[(7-Fluoro-3,4-dihydro-2H-chromen-4-yl)oxy]-N,N,1,2-tetramethyl-1H-benzimidazole-6-carboxamide The title compound was prepared as a white solid in 45% yield (0.96 g) from 4-hydroxy-N,N,1,2-tetramethyl-1H-benzimidazole-6-carboxamide (1.3 g, 5.5 mmol, WO 2004054984) and 4-chloro-7-fluorochromane (2.0 g, 11 mmol, STEP 2) by the same manner in STEP 1 of Example 1:
$^1$H NMR (CDCl$_3$) δ: 7.33-7.23 (m, 1H), 7.11 (d, J=1.3 Hz, 1H), 6.83 (d, J=1.3 Hz, 1H), 6.62-6.52 (m, 2H), 5.98 (t, J=3.3 Hz, 1H), 4.52-4.39 (m, 1H), 4.32-4.22 (m, 1H), 3.73 (s, 3H), 3.11 (s, 3H), 3.02 (s, 3H), 2.62 (s, 3H), 2.42-2.30 (m, 1H), 2.25-2.10 (m, 1H) ppm;
MS (ESI): 384 (M+H)$^+$.

Example 3

(−)-4-[(7-Fluoro-3,4-dihydro-2H-chromen-4-yl)oxy]-N,N,1,2-tetramethyl-1H-benzimidazole-6-carboxamide (fraction-1) and

Example 4

(+)-4-[(7-Fluoro-3,4-dihydro-2H-chromen-4-yl)oxy]-N,N,1,2-tetramethyl-1H-benzimidazole-6-carboxamide (fraction-2)

The fraction-1 (337 mg) and fraction-2 (372 mg) were prepared from racemic 4-[(7-fluoro-3,4-dihydro-2H-chromen-4-yl)oxy]-N,N,1,2-tetramethyl-1H-benzimidazole-6-carboxamide (960 mg, STEP 3 of Example 2) by HPLC as follows.

Isolation Condition
Column: CHIRALCEL OJ-H (20 mm×250 mm, DAICEL)
Mobile phase: n-Hexane/Ethanol/Diethylamine (85/15/0.1)
Flow rate: 18.9 mL/min (−)-4-[(7-Fluoro-3,4-dihydro-2H-chromen-4-yl)oxy]-N,N,1,2-tetramethyl-1H-benzimidazole-6-carboxamide (fraction-1)

NMR: spectrum data were identical with those of the racemate
optical rotation: $[\alpha]_D^{24}$=−129.4° (C=1.11, Methanol)
retention time: 16.7 min (+)-4-[(7-Fluoro-3,4-dihydro-2H-chromen-4-yl)oxy]-N,N,1,2-tetramethyl-1H-benzimidazole-6-carboxamide (fraction-2)

NMR: spectrum data were identical with those of the racemate
optical rotation: $[\alpha]_D^{24}$=+124.0° (C=1.07, Methanol)
retention time: 21.0 min

Example 5

4-[(5,7-Difluoro-3,4-dihydro-2H-chromen-4-yl)oxy]-N,N,1,2-tetramethyl-1H-benzimidazole-6-carboxamide

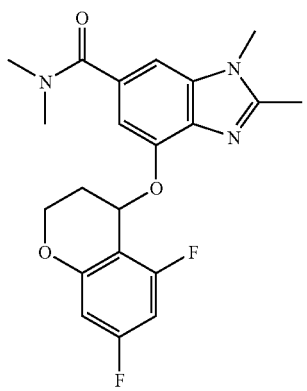

Step 1: 5,7-Difluorochroman-4-ol

The title compound was prepared as a white solid in 68% yield (9.6 g) from 5,7-difluoro-2,3-dihydro-4H-chromen-4-one (14 g, 77 mmol, US 20050038032) by the same manner in STEP 1 of Example 2:
$^1$H NMR (CDCl$_3$) δ: 6.47-6.36 (m, 2H), 5.05-4.97 (m, 1H), 4.36-4.20 (m, 2H), 2.16-1.92 (m, 3H) ppm.

Step 2: 4-Chloro-5,7-difluorochromane

The title compound was prepared as a green oil in 94% yield (9.0 g) from 5,7-difluorochroman-4-ol (8.6 g, 46 mmol, STEP 1) by the same manner in STEP 2 of Example 2:
$^1$H NMR (CDCl$_3$) δ: 6.47-6.35 (m, 2H), 5.36-5.31 (m, 1H), 4.56-4.36 (m, 2H), 2.48-2.23 (m, 2H) ppm.

STEP 3: 4-[(5,7-Difluoro-3,4-dihydro-2H-chromen-4-yl)oxy]-N,N,1,2-tetramethyl-1H-benzimidazole-6-carboxamide The title compound was prepared as a white solid in 49% yield (0.12 g) from 4-hydroxy-N,N,1,2-tetramethyl-1H-benzimidazole-6-carboxamide (0.14 g, 0.61 mmol, WO 2004054984) and 4-chloro-5,7-difluorochromane (0.15 g, 0.73 mmol, STEP 2) by the same manner in STEP 1 of Example 1:
$^1$H NMR (CDCl$_3$) δ: 7.08 (s, 1H), 6.90 (s, 1H), 6.48-6.32 (m, 2H), 6.08-6.00 (m, 1H), 4.55-4.42 (m, 1H), 4.35-4.24 (m, 1H), 3.71 (s, 3H), 3.09 (s, 6H), 2.60 (s, 3H), 2.45-2.33 (m, 1H), 2.17-1.97 (m, 1H) ppm;
MS (ESI): 402 (M+H)$^+$.

Example 6

(−)-4-[(5,7-Difluoro-3,4-dihydro-2H-chromen-4-yl)oxy]-N,N,1,2-tetramethyl-1H-benzimidazole-6-carboxamide and

Example 7

(+)-4-[(5,7-Difluoro-3,4-dihydro-2H-chromen-4-yl)oxy]-N,N,1,2-tetramethyl-1H-benzimidazole-6-carboxamide The fraction-1 (1.13 g) and fraction-2 (1.09 g) were prepared from racemic 4-[(5,7-difluoro-3,4-dihydro-2H-chromen-4-yl)oxy]-N,N,1,2-tetramethyl-1H-benzimidazole-6-carboxamide (3.05 g, STEP 3 of Example 5) by HPLC as follows.

Isolation Condition
Column: CHIRALPAK AD-H (20 mm×250 mm, DAICEL)
Mobile phase: n-Hexane/Ethanol/Diethylamine (80/20/0.1)
Flow rate: 18.9 mL/min (−)-4-[(5,7-Difluoro-3,4-dihydro-2H-chromen-4-yl)oxy]-N,N,1,2-tetramethyl-1H-benzimidazole-6-carboxamide (fraction-1)

NMR: spectrum data were identical with those of the racemate
optical rotation: $[\alpha]_D^{24}$=−119.3° (C=1.00, Methanol)
retention time: 9.4 min (+)-4-[(5,7-Difluoro-3,4-dihydro-2H-chromen-4-yl)oxy]-N,N,1,2-tetramethVl-1H-benzimidazole-6-carboxamide (fraction-2)

NMR: spectrum data were identical with those of the racemate
optical rotation: $[\alpha]_D^{24}$=+116.7° (C=1.00, Methanol)
retention time: 21.1 min

Example 8

N,N,1,2-Tetramethyl-4-[(5-methyl-3,4-dihydro-2H-chromen-4-yl)oxy]-1H-benzimidazole-6-carboxamide

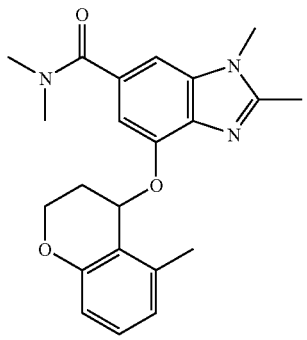

Step 1: 5-Methylchroman-4-ol

The title compound was prepared as a white solid in 99% yield (4.9 g) from 5-methyl-2,3-dihydro-4H-chromen-4-one (4.9 g, 30 mmol, *Synth. Commun.*, 2004, 1691.) by the same manner in STEP 1 of Example 2:
$^1$H NMR (CDCl$_3$) δ: 7.12 (t, J=7.9 Hz, 1H), 6.81-6.69 (m, 2H), 4.91-4.83 (m, 1H), 4.36-4.12 (m, 2H), 2.43 (s, 3H), 2.16-1.98 (m, 2H), 1.75 (d, J=5.3 Hz, 1H) ppm.

Step 2: 4-Chloro-5-methylchromane

The title compound was prepared as a colorless oil in quantitative yield (2.2 g) from 5-methylchroman-4-ol (1.86 g, 11 mmol, STEP 1) by the same manner in STEP 2 of Example 2:
$^1$H NMR (CDCl$_3$) δ: 7.18-7.09 (m, 1H), 6.80-6.62 (m, 2H), 5.36-5.22 (m, 1H), 4.61-4.32 (m, 2H), 2.51-2.28 (m, 2H), 2.41 (s, 3H) ppm.

Step 3: N,N,1,2-Tetramethyl-4-[(5-methyl-3,4-dihydro-2H-chromen-4-yl)oxy]-1H-benzimidazole-6-carboxamide The title compound was prepared as a white solid in 50% yield (116 mg) from 4-hydroxy-N,N,1,2-tetramethyl-1H-benzimidazole-6-carboxamide (100 mg, 0.61 mmol, WO 2004054984) and 4-chloro-5-methylchromane (191 mg, 1.0 mmol, STEP 2) by the same manner in STEP 1 of Example 1:
$^1$H NMR (CDCl$_3$) δ: 7.14 (t, J=8.1 Hz, 1H), 7.08 (s, 1H), 6.91 (s, 1H), 6.78-6.73 (m, 2H), 6.02-5.95 (m, 1H), 4.42-4.30 (m, 1H), 4.27-4.17 (m, 1H), 3.72 (s, 3H), 3.25-2.98 (m, 6H), 2.60 (s, 3H), 2.40-2.35 (m, 1H), 2.31 (s, 3H), 2.20-2.07 (m, 1H) ppm;
MS (ESI): 380 (M+H)$^+$.

Example 9

4-[(5-Fluoro-3,4-dihydro-2H-chromen-4-yl)oxy]-N,N,1,2-tetramethyl-1H-benzimidazole-6-carboxamide

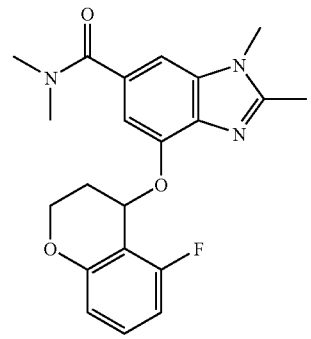

Step 1: 5-Fluorochroman-4-ol

The title compound was prepared as a black oil in quantitative yield (0.9 g) from 5-fluoro-2,3-dihydro-4H-chromen-4-one (0.9 g, 5 mmol, GB 2355264) by the same manner in STEP 1 of Example 2:
$^1$H NMR (CDCl$_3$) δ: 7.25-7.11 (m, 1H), 6.75-6.60 (m, 2H), 5.13-5.02 (m, 1H), 4.40-4.18 (m, 2H), 2.25-1.95 (m, 3H) ppm.

Step 2: 4-Chloro-5-fluorochromane

The title compound was prepared as a black oil in 90% yield (0.92 g) from 5-fluorochroman-4-ol (0.92 g, 5.5 mmol, STEP 1) by the same manner in STEP 2 of Example 2:
$^1$H NMR (CDCl$_3$) δ: 7.24-7.13 (m, 1H), 6.70-6.59 (m, 2H), 5.45-5.36 (m, 1H), 4.56-4.34 (m, 2H), 2.50-2.24 (m, 2H) ppm.

Step 3: 4-[(5-Fluoro-3,4-dihydro-2H-chromen-4-yl)oxy]-N,N,1,2-tetramethyl-1H-benzimidazole-6-carboxamide The title compound was prepared as a pale brown solid in 35% yield (69 mg) from 4-hydroxy-N,N,1,2-tetramethyl-1H-benzimidazole-6-carboxamide (120 mg, 0.51 mmol, WO 2004054984) and 4-chloro-5-fluorochromane (100 mg, 0.54 mmol, STEP 2) by the same manner in STEP 1 of Example 1:
$^1$H NMR (CDCl$_3$) δ: 7.25-7.14 (m, 1H), 7.08 (d, J=1.3 Hz, 1H), 6.92 (d, J=1.3 Hz, 1H), 6.70 (d, J=8.6 Hz, 1H), 6.60 (t, J=8.6 Hz, 1H), 6.10-6.03 (m, 1H), 4.55-4.41 (m, 1H), 4.34-4.24 (m, 1H), 3.71 (s, 3H), 3.11 (s, 3H), 3.07 (s, 3H), 2.59 (s, 3H), 2.45-2.33 (m, 1H), 2.18-2.02 (m, 1H) ppm;
MS (ESI): 384 (M+H)$^+$.

Example 10

4-(3,4-Dihydro-1H-isochromen-4-yloxy)-N,N,1,2-tetramethvl-1H-benzimidazole-6-carboxamide

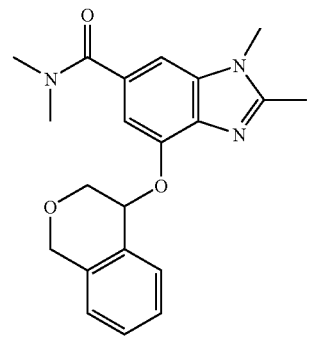

Step 1: 4-Chloro-3,4-dihydro-1H-isochromene

The title compound was prepared as a yellow oil in 99% yield (6.6 g) from 3,4-dihydro-1H-isochromen-4-ol (5.9 g, 39 mmol, WO 2004024081) by the same manner in STEP 2 of Example 2:

$^1$H NMR (CDCl$_3$) δ: 7.54-7.42 (m, 1H), 7.35-7.22 (m, 2H), 7.08-6.97 (m, 1H), 5.18-5.08 (m, 1H), 4.91 (d, J=15.0 Hz, 1H), 4.78 (d, J=15.2 Hz, 1H), 4.27-4.08 (m, 2H) ppm.

Step 2: 4-(3,4-Dihydro-1H-isochromen-4-yloxy)-N,N,1,2-tetramethyl-1H-benzimidazole-6-carboxamide The title compound was prepared as a white solid in 12% yield (38 mg) from 4-hydroxy-N,N,1,2-tetramethyl-1H-benzimidazole-6-carboxamide (0.20 g, 0.85 mmol, WO 2004054984) and 4-chloro-3,4-dihydro-1H-isochromene (0.20 g, 1.2 mmol, STEP 1) by the same manner in STEP 1 of Example 1:

$^1$H NMR (CDCl$_3$) δ: 7.50 (d, J=7.3 Hz, 1H), 7.34-7.17 (m, 2H), 7.14 (s, 1H), 7.06 (d, J=7.3 Hz, 1H), 6.88 (s, 1H), 6.09-6.00 (m, 1H), 4.91 (d, J=15.1 Hz, 1H), 4.77 (d, J=15.1 Hz, 1H), 4.32 (dd, J=12.5, 4.0 Hz, 1 H), 4.11 (dd, J=12.5, 3.3 Hz, 1H), 3.72 (s, 3H), 3.09 (s, 3H), 3.02 (s, 3H), 2.61 (s, 3H) ppm;

MS (ESI): 366 (M+H)$^+$, 364 (M−H)$^−$.

Example 11

4-(3,4-Dihydro-2H-chromen-4-yloxy)-N-(2-hydroxyethyl)-N,1,2-trimethyl-1H-benzimidazole-6-carboxamide

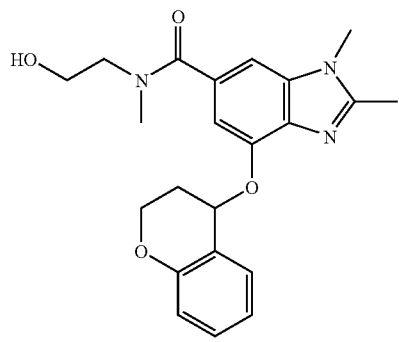

Step 1: Methyl 4-(3,4-dihydro-2H-chromen-4-yloxy)-1,2-dimethyl-1H-benzimidazole-6-carboxylate To a suspension of sodium hydride (60% dispersion in mineral oil, 0.71 g, 18 mmol) in N,N-dimethylformamide (40 mL) was added a suspension of methyl 4-hydroxy-1,2-dimethyl-1H-benzimidazole-6-carboxylate (3.0 g, 14 mmol, WO 2004054984) in N,N-dimethylformamide (40 mL) dropwise under nitrogen atmosphere at room temperature. After stirring for 20 minutes, a solution of 4-chlorochromane (4.6 g, 27 mmol, WO 2000078751) in N,N-dimethylformamide (10 mL) was added at room temperature. The reaction mixture was warmed to 70° C. for 2.5 hours, cooled to room temperature, and stirred for 18 hours at the same temperature. The reaction mixture was quenched with water and extracted with ethyl acetate (250 mL×2). The combined extracts were washed with sodium hydrogencarbonate aqueous solution, ammonium chloride aqueous solution and brine, dried over sodium sulfate, and concentrated in vacuum. The resulting solid was suspended with ethyl acetate and diethyl ether, and collected by filtration to give the title compound as a white solid (2.95 g, 61%):

$^1$H NMR (CDCl$_3$) δ: 7.75 (s, 1H), 7.55 (s, 1H), 7.36 (dd, J=7.9, 1.3 Hz, 1H), 7.27-7.15 (m, 1H), 6.90-6.80 (m, 2H), 5.96-5.90 (m, 1H), 4.52-4.40 (m, 1H), 4.32-4.25 (m, 1H), 3.95 (s, 3H), 3.77 (s, 3H), 2.63 (s, 3H), 2.42-2.20 (m, 2H) ppm;

MS (ESI): 353 (M+H)$^+$.

Step 2: 4-(3,4-Dihydro-2H-chromen-4-yloxy)-1,2-dimethyl-1H-benzimidazole-6-carboxylic acid To a stirred solution of methyl 4-(3,4-dihydro-2H-chromen-4-yloxy)-1,2-dimethyl-1H-benzimidazole-6-carboxylate (1.0 g, 2.8 mmol, STEP 1) in methanol (20 mol) and tetrahydrofuran (30 mL) was added 4M lithium hydroxide aqueous solution (4 mL, 16 mmol) at room temperature. After stirring for 5 hours at 60° C., the reaction mixture was concentrated in vacuum. The residue was dissolved with water and acidified (pH=3) with 2M hydrochloric acid. The resulting precipitate was filtered, and dried in vacuum to afford the title compound as a white solid (0.85 g, 89%):

$^1$H NMR (CDCl$_3$) δ: 7.81 (s, 1H), 7.62 (s, 1H), 7.38-7.34 (m, 1H), 7.27-7.18 (m, 1H), 6.90-6.83 (m, 2H), 5.93-5.90 (m, 1H), 4.53-4.50 (m, 1H), 4.32-4.26 (m, 1H), 3.80 (s, 3H), 2.68 (s, 3H), 2.40-2.10 (m, 2H) ppm (—OH was not observed);

MS (ESI): 339 (M+H)$^+$, 337 (M−H)$^−$.

Step 3: 4-(3,4-Dihydro-2H-chromen-4-yloxy)-N-(2-hydroxyethyl)-N,1,2-trimethyl-1H-benzimidazole-6-carboxamide To a stirred mixture of 4-(3,4-dihydro-2H-chromen-4-yloxy)-1,2-dimethyl-1H-benzimidazole-6-carboxylic acid (70 mg, 0.21 mmol, STEP 2) and 2-(methylamino)ethanol (31 mg, 0.41 mmol) in dimethylformamide (2 mL) were added 1-(3-dimethylaminopropyl)-3-ethylcarbodiimide hydrochloride (EDCl) (67 mg, 0.35 mmol) and 1-hydroxybenzotriazole hydrate (HOBt) (60 mg, 0.41 mmol) at room temperature. After stirring at room temperature for 18 hours, the reaction mixture was quenched with sodium hydrogencarbonate aqueous solution (5 mL), and extracted with ethyl acetate (50 mL×2). The combined extracts were washed with brine, dried over sodium sulfate, and concentrated in vacuum. The residue was purified by column chromatography on silica gel (ethyl acetate:methanol=10:1 as an eluent). The residue was suspended with diethyl ether, and collected by filtration to afford the title compound as a white solid (24 mg, 24%):

$^1$H NMR (CDCl$_3$) δ: 7.30-7.16 (m, 3H), 6.92-6.82 (m, 3H), 6.02-5.97 (m, 1H), 4.50-4.43 (m, 1H), 4.33-4.23 (m, 1H), 3.95-3.88 (m, 2H), 3.75-3.50 (m, 2H), 3.73 (s, 3H), 3.07 (s, 3H), 2.62 (s, 3H), 2.40-2.34 (m, 1H), 2.28-2.18 (m, 1H) ppm (—OH was not observed);

MS (ESI): 396 (M+H)$^+$.

Example 12

(3S)-1-{[4-(3,4-Dihydro-2H-chromen-4-yloxy)-1,2-dimethyl-1H-benzimidazol-6-yl]carbonyl}pyrrolidin-3-ol

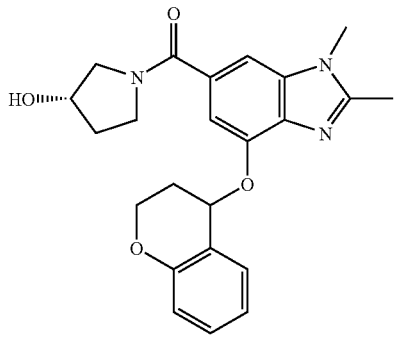

The title compound was prepared as a white solid in 25% yield (30 mg) from 4-(3,4-dihydro-2H-chromen-4-yloxy)-1,2-dimethyl-1H-benzimidazole-6-carboxylic acid (100 mg, 0.30 mmol, STEP 2 of Example 11) and (S)-(+)-3-pyrrolidinol (77 mg, 0.63 mmol) by the same manner in STEP 3 of Example 11:

$^1$H NMR (CDCl$_3$) δ: 7.28-7.18 (m, 3H), 6.98-6.82 (m, 3H), 6.02-5.91 (m, 1H), 4.62-4.58 (m, 1H), 4.49-4.40 (m, 1H), 4.33-4.24 (m, 1H), 3.90-3.62 (m, 2H), 3.72 (s, 3H), 3.60-3.31 (m, 2H), 2.62 (s, 3H), 2.44-2.30 (m, 1H), 2.30-2.12 (m, 1H), 2.11-1.85 (m, 2H) ppm (—OH was not observed);

MS (ESI): 408 (M+H)$^+$.

Example 13

(3R)-1-{[4-(3,4-Dihydro-2H-chromen-4-yloxy)-1,2-dimethyl-1H-benzimidazol-6-yl]carbonyl}pyrrolidin-3-ol

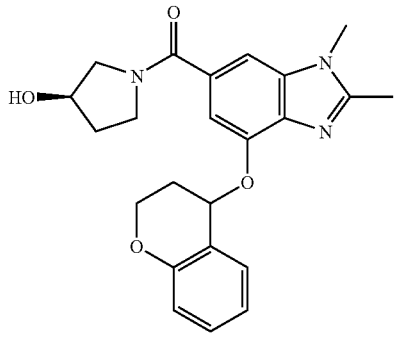

The title compound was prepared as a white solid in 23% yield (19 mg) from 4-(3,4-dihydro-2H-chromen-4-yloxy)-1,2-dimethyl-1H-benzimidazole-6-carboxylic acid (70 mg, 0.21 mmol, STEP 2 of Example 11) and (R)-(−)-3-pyrrolidinol (77 mg, 0.63 mmol) by the same manner in STEP 3 of Example 11:

$^1$H NMR (CDCl$_3$) δ: 7.33-7.17 (m, 3H), 7.01-6.80 (m, 3H), 6.04-5.93 (m, 1H), 4.63-4.58 (m, 1H), 4.51-4.37 (m, 1H), 4.32-4.21 (m, 1H), 3.93-3.32 (m, 4H), 3.73 (m, 3H), 2.62 (s, 3H), 2.44-2.30 (m, 1H), 2.30-1.91 (m, 3H), 1.85-1.70 (m, 1H) ppm;

MS (ESI): 408 (M+H)$^+$.

Example 14

(2R)-1-{[4-(3,4-Dihydro-2H-chromen-4-yloxy)-1,2-dimethyl-1H-benzimidazol-6-yl]carbonyl}pyrrolidin-2-yl)methanol

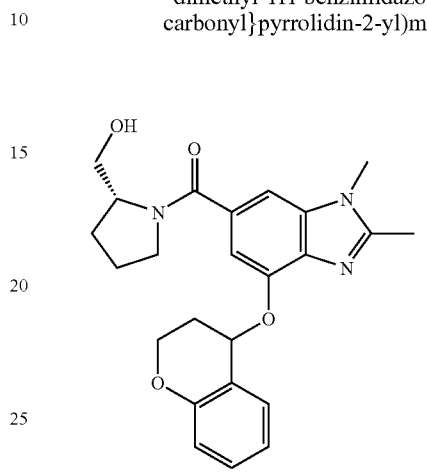

The title compound was prepared as a white solid in 57% yield (50 mg) from 4-(3,4-dihydro-2H-chromen-4-yloxy)-1,2-dimethyl-1H-benzimidazole-6-carboxylic acid (70 mg, 0.21 mmol, STEP 2 of Example 11) and (R)-(−)-2-pyrrolidinemethanol (41 mg, 0.42 mmol) by the same manner in STEP 3 of Example 11:

$^1$H NMR (CDCl$_3$) δ: 7.32-7.18 (m, 3H), 6.96-6.80 (m, 3H), 6.08-5.99 (m, 1H), 5.10-4.94 (m, 1H), 4.53-4.35 (m, 2H), 4.82-4.25 (m, 1H), 3.89-3.69 (m, 2H), 3.74 (s, 3H), 3.65-3.33 (m, 2H), 2.63 (s, 3H), 2.46-2.31 (m, 1H), 2.30-2.11 (m, 2H), 1.94-1.60 (m, 3H) ppm;

MS (ESI): 422 (M+H)$^+$.

Example 15

4-(3,4-Dihydro-2H-chromen-4-yloxy)-1,2-dimethyl-6-[(4-methylpiperazin-1-yl)carbonyl]-1H-benzimidazole

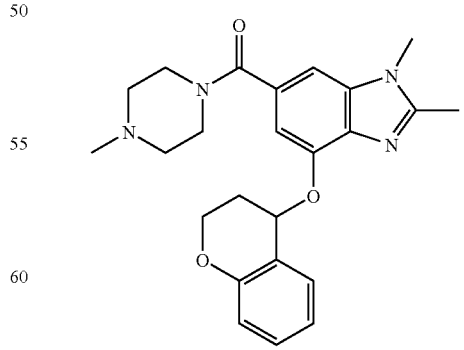

The title compound was prepared as a white solid in 34% yield (30 mg) from 4-(3,4-dihydro-2H-chromen-4-yloxy)-1,2-dimethyl-1H-benzimidazole-6-carboxylic acid (70 mg, 0.21 mmol, STEP 2 of Example 11) and 1-methylpiperazine (41 mg, 0.42 mmol) by the same manner in STEP 3 of Example 11:

$^1$H NMR (CDCl$_3$) δ: 7.27-7.20 (m, 2H), 7.10 (s, 1H), 6.89-6.80 (m, 3H), 6.05-6.00 (m, 1H), 4.45-4.43 (m, 1H), 4.32-4.25 (m, 1H), 3.80-3.55 (m, 2H), 3.74 (s, 3H), 3.52-3.45 (m, 2H), 2.62 (s, 3H), 2.45-2.21 (m, 6H), 2.32 (s, 3H) ppm.

MS (ESI): 421 (M+H)$^+$.

Example 16

6-[(4-Acetylpiperazin-1-yl)carbonyl]-4-(3,4-dihydro-2H-chromen-4-yloxy)-1,2-dimethyl-1H-benzimidazole

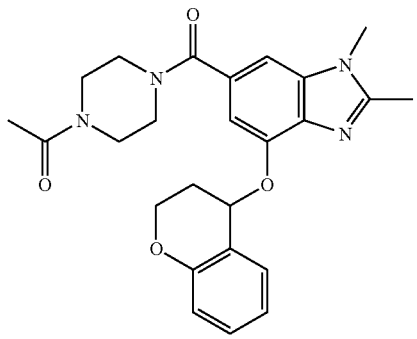

The title compound was prepared as a white solid in 38% yield (35 mg) from 4-(3,4-dihydro-2H-chromen-4-yloxy)-1,2-dimethyl-1H-benzimidazole-6-carboxylic acid (70 mg, 0.21 mmol, STEP 2 in Example 11) and 1-acetylpiperazine (53 mg, 0.42 mmol) by the same manner in STEP 3 in Example 11: $^1$H NMR (CDCl$_3$) δ: 7.31-7.23 (m, 2H), 7.21 (s, 1H), 6.89-6.77 (m, 3H), 6.50-6.00 (m, 1H), 4.50-4.40 (m, 1H), 4.27-4.32 (m, 1H), 3.75 (s, 3H), 3.80-3.36 (m, 8H), 2.64 (s, 3H), 2.40-2.19 (m, 2H), 2.13 (s, 3H) ppm;

MS (ESI): 449 (M+H)$^+$.

Example 17

(−)-4-{[5-Fluoro-3,4-dihydro-2H-chromen-4-yl]oxy}-N,N,1,2-tetramethyl-1H-benzimidazole-6-carboxamide and Example 18

(+)-4-{[5-Fluoro-3,4-dihydro-2H-chromen-4-yl]oxy}-N,N,1,2-tetramethyl-1H-benzimidazole-6-carboxamide The fraction-1 (315 mg) and fraction-2 (307 mg) were prepared from racemic 4-{[5-fluoro-3,4-dihydro-2H-chromen-4-yl]oxy}-N,N,1,2-tetramethyl-1H-benzimidazole-6-carboxamide (750 mg, STEP 3 of Example 9) by HPLC as follows.

Isolation Condition
Column: CHIRALCEL OJ-H (20 mm×250 mm, DAICEL)
Mobile phase: n-Hexane/Ethanol/Diethylamine (85/15/0.1)
Flow rate: 18.9 mL/min (−)-4-{[5-Fluoro-3,4-dihydro-2H-chromen-4-yl]oxy}-N,N,1 2-tetramethyl-1H-benzimidazole-6-carboxamide (fraction-1)

NMR: spectrum data were identical with those of the racemate
optical rotation: [α]$_D^{21}$=−124.3° (C=1.00, Methanol)
retention time: 18 min (+)-4-{[5-Fluoro-3,4-dihydro-2H-chromen-4-yl]oxy}-N,N,1,2-tetramethyl-1H-benzimidazole-6-carboxamide (fraction-2)

NMR: spectrum data were identical with those of the racemate
optical rotation: [α]$_D^{21}$=+125.8° (C=1.01, Methanol)
retention time: 23 min Example 19

4-[(5,7-Difluoro-3,4-dihydro-2H-chromen-4-yl)oxy]-N,1,2-trimethyl-1H-benzimidazole-6-carboxamide

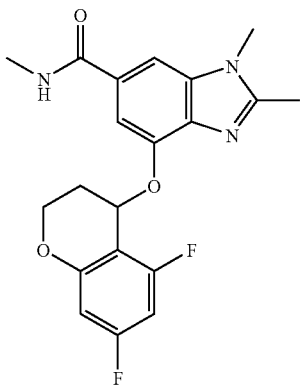

Step1: Methyl 4-[(5,7-difluoro-3,4-dihydro-2H-chromen-4-yl)oxy]-1,2-dimethyl-1H-benzimidazole-6-carboxylate The title compound was prepared as a white solid in 59% yield (3.2 g) from methyl 4-hydroxy-1,2-dimethyl-1H-benzimidazole-6-carboxylate (3.0 g, 14 mmol, WO 2004054984) and 4-chloro-5,7-difluorochromane (4.7 g, 21 mmol, STEP 2 of Example 5) by the same manner in STEP 1 of Example 11.

$^1$H NMR (CDCl$_3$) δ: 7.74 (s, 1H), 7.57 (s, 1H), 6.46-6.33 (m, 2H), 6.01-6.04 (m, 1H), 4.55-4.44 (m, 1H), 4.33-4.24 (m, 1H), 3.96 (s, 3H), 3.76 (s, 3H), 2.62 (s, 3H), 2.44-2.36 (m, 1H), 2.19-2.04 (m, 1H) ppm;

MS (ESI): 389 (M+H)$^+$.

Step 2: 4-[(5,7-Difluoro-3,4-dihydro-2H-chromen-4-yl)oxy]-1,2-dimethyl-1H-benzimidazole-6-carboxylic acid The title compound was prepared as a white solid in 88% yield (2.7 g) from methyl 4-[(5,7-difluoro-3,4-dihydro-2H-chromen-4-yl)oxy]-1,2-dimethyl-1H-benzimidazole-6-carboxylate (3.2 g, 8.2 mmol, STEP 1) by the same manner in STEP 2 of Example 11.

¹H NMR (DMSO-d₆) δ: 12.8 (br s, 1H), 7.79 (s, 1H), 7.40 (s, 1H), 6.86-6.80 (m, 1H), 6.73-6.68 (m, 1H), 6.16-6.14 (m, 1H), 4.40-4.19 (m, 2H), 3.77 (s, 3H), 2.50 (s, 3H), 2.27-2.00 (m, 2H) ppm;
MS (ESI): 375 (M+H)⁺, 373 (M−H)⁻.

Step 3: 4-[(5,7-Difluoro-3,4-dihydro-2H-chromen-4-yl)oxy]-N,1,2-trimethyl-1H-benzimidazole-6-carboxamide The title compound was prepared as a colorless amorphous in 96% yield (0.99 g) from 4-[(5,7-difluoro-3,4-dihydro-2H-chromen-4-yl)oxy]-1,2-dimethyl-1H-benzimidazole-6-carboxylic acid (1.0 g, 2.7 mmol, STEP 2) and methanamine hydrochloride (0.54 g, 8.0 mmol) by the same manner in STEP 3 of Example 11.
¹H NMR (CDCl₃) δ: 7.43 (d, J=1.5 Hz, 1H), 7.23 (d, J=1.5 Hz, 1H), 6.47-6.32 (m, 3H), 6.10-6.05 (m, 1H), 4.52-4.40 (m, 1H), 4.34-4.24 (m, 1H), 3.69 (s, 3H), 3.04 (d, J=5.1 Hz, 3H), 2.58 (s, 3H), 2.43-2.33 (m, 1H), 2.15-2.00 (m, 1H) ppm;
MS (ESI): 388 (M+H)⁺, 386 (M−H)⁻.

Example 20

(−)-4-[(5,7-Difluoro-3,4-dihydro-2H-chromen-4-yl)oxy]-N,1,2-trimethyl-1H-benzimidazole-6-carboxamide and Example 21

(+)-4-[(5,7-Difluoro-3,4-dihydro-2H-chromen-4-yl)oxy]-N,1,2-trimethyl-1H-benzimidazole-6-carboxamide The fraction-1 (0.42 g) and fraction-2 (0.43 g) were prepared from racemic 4-[(5,7-difluoro-3,4-dihydro-2H-chromen-4-yl)oxy]-N,1,2-trimethyl-1H-benzimidazole-6-carboxamide (0.99 g, STEP 3 of Example 19) by HPLC as follows.

Isolation Condition
Column: CHIRALPAK AD-H (20 mm×250 mm, DAICEL)
Mobile phase: n-Hexane/Ethanol/Diethylamine (85/15/0.1)
Flow rate: 18.9 mL/min (−)-4-[(5,7-Difluoro-3,4-dihydro-2H-chromen-4-yl)oxy]-N,1,2-trimethyl-1H-benzimidazole-6-carboxamide (fraction-1)

NMR: spectrum data were identical with those of the racemate
optical rotation: $[\alpha]_D^{24}$=−111.9° (C=0.50, Methanol)
retention time: 10 min (+)-4-[(5,7-Difluoro-3,4-dihydro-2H-chromen-4-yl)oxy]-N,1,2-trimethyl-1H-benzimidazole-6-carboxamide (fraction-2)

NMR: spectrum data were identical with those of the racemate
optical rotation: $[\alpha]_D^{24}$=+110.7° (C=0.50, Methanol)
retention time: 14 min Example 22

6-(Azetidin-1-ylcarbonyl)-4-[(5,7-difluoro-3,4-dihydro-2H-chromen-4-yl)oxy]-1,2-dimethyl-1H-benzimidazole

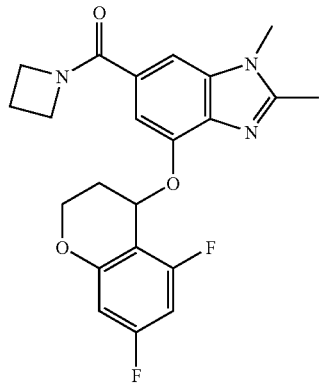

The title compound was prepared as a colorless amorphous in 80% yield (1.4 g) from 4-[(5,7-difluoro-3,4-dihydro-2H-chromen-4-yl)oxy]-1,2-dimethyl-1H-benzimidazole-6-carboxylic acid (1.6 g, 4.2 mmol, STEP 2 of Example 19) and azetidine hydrochloride (0.79 g, 8.4 mmol) by the same manner in STEP 3 of Example 11.
¹H NMR (CDCl₃) δ: 7.33 (d, J=1.5 Hz, 1H), 7.11 (d, J=1.5 Hz, 1H), 6.48-6.32 (m, 2H), 6.03-5.98 (m, 1H), 4.56-4.42 (m, 1H), 4.41-4.20 (m, 5H), 3.72 (s, 3H), 2.60 (s, 3H), 2.46-2.30 (m, 3H), 2.16-2.01 (m, 1H) ppm;
MS (ESI): 414 (M+H)⁺.

Example 23

(−)-6-(Azetidin-1-ylcarbonyl)-4-[(5,7-difluoro-3,4-dihydro-2H-chromen-4-yl)oxy]-1,2-dimethyl-1H-benzimidazole and Example 24

(+)-6-(Azetidin-1-ylcarbonyl)-4-[(5,7-difluoro-3,4-dihydro-2H-chromen-4yl)oxy]-1,2-dimethyl-1H-benzimidazole The fraction-1 (0.48 g) and fraction-2 (0.48 g) were prepared from racemic 6-(azetidin-1-ylcarbonyl)-4-[(5,7-difluoro-3,4-dihydro-2H-chromen-4-yl)oxy]-1,2-dimethyl-1H-benzimidazole (1.4 g, Example 22) by HPLC as follows.

Isolation Condition
Column: CHIRALPAK AD-H (20 mm×250 mm, DAICEL)
Mobile phase: n-Hexane/Ethanol/Diethylamine (80/20/0.1)
Flow rate: 20 mL/min (−)-6-(Azetidin-1-ylcarbonyl)-4-[(5,7-difluoro-3,4-dihydro-2H-chromen-4-yl)oxy]-1,2-dimethyl-1H-benzimidazole (fraction-1)

NMR: spectrum data were identical with those of the racemate
optical rotation: $[\alpha]_D^{21}$=−113.6° (C=0.48, Methanol)
retention time: 15 min (+)-6-(Azetidin-1-ylcarbonyl)-4-[(5,7-difluoro-3,4-dihydro-2H-chromen-4-yl)oxy]-1,2-dimethyl-1H-benzimidazole (fraction-2)

NMR: spectrum data were identical with those of the racemate
optical rotation: $[\alpha]_D^{22}=+119.8°$ (C=0.49, Methanol)
retention time: 26 min Example 25

4-[(5,7-Difluoro-3,4-dihydro-2H-chromen-4-yl)oxy]-1,2-dimethyl-6-(pyrrolidin-1-ylcarbonyl)-1H-benzimidazole

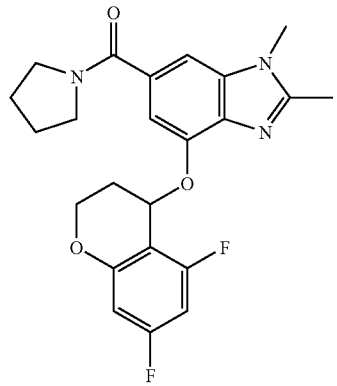

The title compound was prepared as a colorless amorphous in 39% yield (45 mg) from 4-[(5,7-difluoro-3,4-dihydro-2H-chromen-4-yl)oxy]-1,2-dimethyl-1H-benzimidazole-6-carboxylic acid (100 mg, 0.27 mmol, STEP 2 of Example 19) and pyrrolidine (38 mg, 0.53 mmol) by the same manner in STEP 3 of Example 11.
$^1$H NMR (CDCl$_3$) δ: 7.20 (s, 1H), 7.01 (s, 1H), 6.48-6.32 (m, 2H), 6.07-6.00 (m, 1H), 4.55-4.42 (m, 1H), 4.35-4.25 (m, 1H), 3.78-3.63 (m, 2H), 3.72 (s, 3H), 3.55-3.42 (m, 2H), 2.60 (s, 3H), 2.45-2.34 (m, 1H), 2.15-1.80 (m, 5H) ppm;
MS (ESI): 428 (M+H)$^+$.

Example 26

1-({4-[(5,7-Difluoro-3,4-dihydro-2H-chromen-4-yl)oxy]-1,2-dimethyl-1H-benzimidazol-6-yl}carbonyl)-3-methylazetidin-3-ol

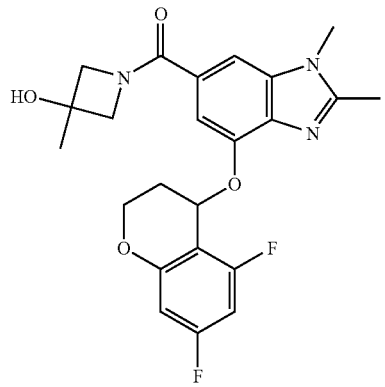

Step1: 3-Methylazetidin-3-ol hydrochloride 1-(Diphenylmethyl)-3-methylazetidin-3-ol (0.48 g, 1.9 mmol) and 10% palladium on activated carbon (0.20 g) in methanol (4 mL) was stirred under hydrogen gas (4 atmospheres) for 10 hours. The resulted mixture was filtered through a pad of Celite. 4M hydrogen chloride in dioxane (1 mL) was added to the filtrate, and the mixture was concentrated in vacuum to afford the title compound as crude oil (0.38 g).

Step2: 1-({4-[(5,7-Difluoro-3,4-dihydro-2H-chromen-4-yl)oxy]-1,2-dimethyl-1H-benzimidazol-6-yl}carbonyl)-3-methylazetidin-3-ol The title compound was prepared as a colorless amorphous in 76% yield (71 mg) from 4-[(5,7-difluoro-3,4-dihydro-2H-chromen-4-yl)oxy]-1,2-dimethyl-1H-benzimidazole-6-carboxylic acid (80 mg, 0.21 mmol, STEP 2 of Example 21) and 3-methylazetidin-3-ol hydrochloride (crude 135 mg, STEP 1) by the same manner in STEP 3 of Example 11.
$^1$H NMR (CDCl$_3$) δ: 7.25-7.15 (m, 1H), 7.11 (br s, 1H), 6.48-6.33 (m, 2H), 6.05-5.98 (m, 1H), 4.53-4.41 (m, 1H), 4.35-4.13 (m, 5H), 3.67 (s, 3H), 2.58 (s, 3H), 2.43-2.32 (m, 1H), 2.16-2.02 (m, 1H), 1.56 (s, 3H) ppm (—OH was not observed.);
MS (ESI): 444 (M+H)$^+$.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:
1. A compound of the formula (I):

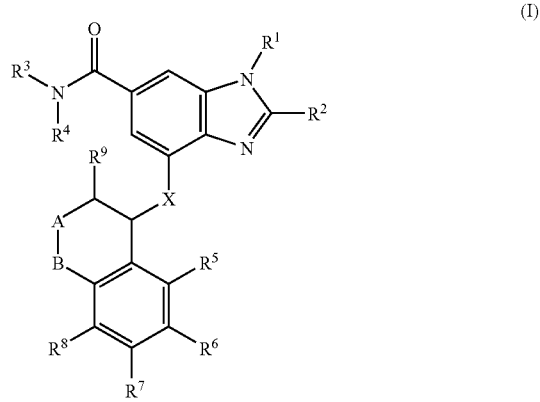

wherein:
-A-B— is —O—CH$_2$—, —S—CH$_2$—, —CH$_2$—O—, or —CH$_2$—S—;
X is an oxygen atom or NH;
R$^1$ and R$^2$ are each independently C$_1$-C$_4$ alkyl each being unsubstituted or substituted with 1 to 2 substituents independently selected from hydroxy or C$_1$-C$_4$ alkoxy;

$R^3$ and $R^4$ are each independently hydrogen, $C_1$-$C_4$ alkyl, or $C_3$-$C_7$ cycloalkyl, said $C_1$-$C_4$ alkyl and said $C_3$-$C_7$ cycloalkyl being unsubstituted or substituted with 1 to 3 substituents independently selected from halogen, hydroxy, $C_1$-$C_4$ alkoxy, or $C_3$-$C_7$ cycloalkyl; or $R^3$ and $R^4$ taken together with the nitrogen atom to which they are attached form a 4 to 6 membered heterocyclic group being unsubstituted or substituted with 1 to 3 substituents selected from hydroxy, $C_1$-$C_4$ alkyl, $C_1$-$C_4$ acyl, or hydroxy-$C_1$-$C_4$ alkyl;

$R^5$, $R^6$, $R^7$, and $R^8$ are each independently hydrogen, halogen, hydroxy, $C_1$-$C_4$ alkyl, or $C_1$-$C_4$ alkoxy; and $R^9$ is hydrogen, hydroxy, or $C_1$-$C_4$ alkoxy; or a pharmaceutically acceptable salt thereof.

2. The compound of claim 1, wherein:

X is an oxygen atom;

$R^3$ and $R^4$ are each independently hydrogen, $C_1$-$C_4$ alkyl, or $C_3$-$C_7$ cycloalkyl, said $C_1$-$C_4$ alkyl and said $C_3$-$C_7$ cycloalkyl being unsubstituted or substituted with 1 to 3 substituents independently selected from hydrogen, hydroxyl, $C_1$-$C_4$ alkoxy, or $C_3$-$C_7$ cycloalkyl; or $R^3$ and $R^4$ taken together with the nitrogen atom to which they are attached form an azetidinyl, pyrrolidinyl, or piperazinyl group, said azetidinyl, pyrrolidinyl group, and piperazinyl groups being unsubstituted or substituted with 1 to 3 substituents selected from hydroxyl, $C_1$-$C_4$ alkyl, $C_1$-$C_4$ acyl, or hydroxyl-$C_1$-$C_4$ alkyl; and $R^6$, $R^8$, and $R^9$ are each hydrogen;

or a pharmaceutically acceptable salt thereof.

3. The compound of claim 1, wherein:

-A-B— is —$CH_2$—O—;

X is oxygen;

$R^1$ and $R^2$ are each methyl;

$R^3$ and $R^4$ are each methyl; or $R^3$ and $R^4$ taken together with the nitrogen atom to which they are attached form an azetidin-1-yl, pyrrolidin-1-yl, 3-hydroxy-pyrrolidin-1-yl, or 4-acetyl-piperazin-1-yl group;

$R^5$ and $R^7$ are independently hydrogen, halogen, or methyl; and $R^6$, $R^8$ and $R^9$ are each a hydrogen atom;

or a pharmaceutically acceptable salt thereof.

4. The compound of claim 1, which is:

4-[(7-Fluoro-3,4-dihydro-2H-chromen-4yl)oxy]-N,N,1,2-tetramethyl-1H-benzimidazole-6-carboxamide;

4-[(5,7-Difluoro-3,4-dihydro-2H-chromen-4-yl)oxy]-N,N,1,2-tetramethyl-1H-benzimidazole-6-carboxamide; or N,N,1,2-Tetramethyl-4-[(5-methyl-3,4-dihydro-2H-chromen-4-yl)oxy]-1H-benzimidazole-6-carboxamide;

or a pharmaceutically acceptable salt thereof.

5. A pharmaceutical composition comprising the compound or the pharmaceutically acceptable salt thereof of claim 1, and at least one pharmaceutically acceptable carrier.

* * * * *